US007927012B2

(12) United States Patent
Harr et al.

(10) Patent No.: US 7,927,012 B2
(45) Date of Patent: Apr. 19, 2011

(54) PROBE COVER CASSETTE WITH IMPROVED PROBE COVER SUPPORT

(75) Inventors: James M. Harr, Foristell, MO (US); Mitchell H. Babkes, Saugus, CA (US); Clarence Walker, St. Louis, MO (US)

(73) Assignee: Covidien AG (CH)

(*) Notice: Subject to any disclaimer, the term of this patent is extended or adjusted under 35 U.S.C. 154(b) by 0 days.

(21) Appl. No.: 12/333,872

(22) Filed: Dec. 12, 2008

(65) Prior Publication Data

US 2009/0092172 A1 Apr. 9, 2009

Related U.S. Application Data

(63) Continuation of application No. 11/419,438, filed on May 19, 2006, now Pat. No. 7,478,946, which is a continuation-in-part of application No. 11/286,620, filed on Nov. 23, 2005, now Pat. No. 7,354,194, which is a continuation-in-part of application No. 10/538,314, filed as application No. PCT/US03/000224 on Jan. 6, 2003, now Pat. No. 7,237,949.

(51) Int. Cl.
*G01K 1/08* (2006.01)

(52) U.S. Cl. ........ 374/158; 374/209; 374/163; 374/121; 600/549

(58) Field of Classification Search .................. 374/158, 374/208, 209, 183, 163, 141; 600/549, 474
See application file for complete search history.

(56) References Cited

U.S. PATENT DOCUMENTS 3,282,106 A 11/1966 Barnes
3,282,458 A 11/1966 Rudd
3,626,758 A 12/1971 Stewart et al.
3,681,991 A 8/1972 Eberly, Jr.
3,738,479 A 6/1973 Sato
3,765,238 A 10/1973 Sumikama et al.
3,822,593 A 7/1974 Oudewaal
3,832,669 A 8/1974 Mueller et al.

(Continued)

FOREIGN PATENT DOCUMENTS

EP 0201790 A1 11/1986

(Continued)

OTHER PUBLICATIONS

European Search Report, Application 07009973.4, dated Aug. 9, 2007, 9 pages.

(Continued)

*Primary Examiner* — Gail Verbitsky
(74) *Attorney, Agent, or Firm* — Lisa E. Winsor, Esq.

(57) ABSTRACT

A cassette of tympanic thermometer probe covers includes a frame and probe covers releasably attached to the frame. The probe covers can be individually attached over a probe of a tympanic thermometer to protect the probe from contamination. The probe covers are constructed to releasably secure themselves to the probe. The force required to secure the probe covers to the frame is less that the force which is required to detach the probe covers from the frame so that the probe cover is held by the frame while being attached to the thermometer probe. The probe cover is connected to the frame by frangible connections that are arranged to inhibit pivoting of the probe cover when being attached to the thermometer probe. A method of securing a probe cover to a probe of a tympanic thermometer is also disclosed.

11 Claims, 27 Drawing Sheets

U.S. PATENT DOCUMENTS 3,872,728 A 3/1975 Joyce et al.
3,905,232 A 9/1975 Knute
3,915,371 A 10/1975 Crabtree
3,942,891 A 3/1976 Spielberger et al.
3,949,740 A 4/1976 Twentier
4,007,832 A 2/1977 Paull et al.
4,008,614 A 2/1977 Turner et al.
4,143,765 A 3/1979 Moss, III
4,159,766 A 7/1979 Kluge
4,349,109 A 9/1982 Scordato et al.
4,457,633 A 7/1984 Andrews
4,497,585 A 2/1985 Paull et al.
4,527,896 A 7/1985 Irani et al.
4,572,365 A 2/1986 Bruno et al.
4,576,486 A 3/1986 Dils
4,602,642 A 7/1986 O'Hara et al.
4,622,360 A 11/1986 Gomi et al.
4,636,091 A 1/1987 Pompei et al.
4,662,360 A 5/1987 O'Hara et al.
4,703,857 A 11/1987 Jahnen et al.
4,770,544 A 9/1988 Mossey
4,784,149 A 11/1988 Berman et al.
4,790,324 A 12/1988 O'Hara et al.
4,854,730 A 8/1989 Fraden
4,911,559 A 3/1990 Meyst et al.
4,993,424 A 2/1991 Suszynski et al.
5,017,018 A 5/1991 Iuchi et al.
5,018,872 A 5/1991 Suszynski et al.
D318,812 S 8/1991 Matsuura
5,046,482 A 9/1991 Everest
5,060,819 A 10/1991 Apps
5,066,142 A 11/1991 DeFrank et al.
5,088,834 A 2/1992 Howe et al.
5,100,018 A 3/1992 Rosati et al.
5,163,418 A 11/1992 Fraden et al.
5,179,936 A 1/1993 O'Hara et al.
5,188,459 A 2/1993 Mino et al.
5,292,001 A 3/1994 Langenbeck et al.
RE34,599 E 5/1994 Suszynski et al.
5,318,029 A 6/1994 Palese
5,364,186 A 11/1994 Wang et al.
5,411,032 A 5/1995 Esseff et al.
5,441,702 A 8/1995 Lemieux et al.
5,487,607 A 1/1996 Makita et al.
5,516,010 A 5/1996 O'Hara et al.
5,518,114 A 5/1996 Kohring et al.
5,588,748 A * 12/1996 Nomura et al. ............... 374/158
5,601,365 A 2/1997 Li
5,609,564 A 3/1997 Makita et al.
5,638,951 A 6/1997 Fukura et al.
5,645,350 A 7/1997 Jang
5,795,067 A 8/1998 Fraden et al.
5,795,632 A 8/1998 Buchalter
5,820,264 A 10/1998 Tsao et al.
5,833,367 A 11/1998 Cheslock et al.
5,836,692 A 11/1998 Pompei
5,906,437 A 5/1999 Lin
5,948,362 A 9/1999 Steinbrenner et al.
5,980,451 A 11/1999 O'Hara et al.
6,001,066 A 12/1999 Canfield et al.
6,022,140 A 2/2000 Fraden et al.
6,030,117 A 2/2000 Cheslock et al.
6,042,266 A 3/2000 Cheslock et al.
6,084,395 A 7/2000 Thiel
6,097,979 A * 8/2000 Janotte .......................... 600/474
6,109,784 A 8/2000 Weiss
6,123,454 A 9/2000 Canfield et al.
6,139,182 A 10/2000 Levatter et al.
6,152,596 A 11/2000 Fraden
6,156,148 A 12/2000 Beerwerth et al.
6,179,785 B1 1/2001 Martinosky et al.
6,186,959 B1 2/2001 Canfield et al.
6,193,411 B1 2/2001 Chen
6,195,581 B1 2/2001 Beerwerth et al.
6,224,256 B1 5/2001 Bala
6,236,880 B1 5/2001 Raylman et al.
6,238,088 B1 5/2001 Wu
6,238,089 B1 5/2001 Vodzak et al.
6,254,271 B1 7/2001 Lin
6,319,206 B1 11/2001 Pompei et al.
6,332,090 B1 12/2001 DeFrank et al.
6,347,243 B1 2/2002 Fraden
6,367,973 B2 4/2002 Yamaka
6,386,757 B1 5/2002 Konno
6,390,671 B1 5/2002 Tseng
6,402,371 B2 6/2002 Pompei et al.
6,416,602 B1 7/2002 Firatli
6,447,160 B1 9/2002 Fraden
6,485,433 B1 11/2002 Peng
6,530,881 B1 3/2003 Ailinger et al.
6,549,794 B1 4/2003 Nadeau, Jr. et al.
6,605,034 B2 8/2003 Hascoet et al.
6,612,735 B2 9/2003 Tomioka et al.
6,634,787 B1 10/2003 Beerwerth et al.
6,647,284 B1 11/2003 Lee
6,694,174 B2 2/2004 Kraus et al.
6,695,474 B2 2/2004 Beerwerth et al.
6,733,464 B2 5/2004 Olbrich et al.
6,749,334 B2 6/2004 Lin
6,761,684 B1 7/2004 Speier
6,773,405 B2 8/2004 Fraden et al.
6,786,636 B1 9/2004 Huang et al.
6,789,936 B1 9/2004 Kraus et al.
6,814,697 B2 11/2004 Ouchi
6,827,486 B2 12/2004 Welker
6,840,402 B2 1/2005 Lin et al.
6,846,105 B2 1/2005 Xie et al.
6,851,850 B1 2/2005 Lee
6,854,880 B2 2/2005 Hsieh
6,855,108 B2 2/2005 Ishibiki et al.
6,869,393 B2 3/2005 Butler
6,908,439 B2 6/2005 Carney
6,911,005 B2 6/2005 Ouchi et al.
6,921,362 B2 7/2005 Ouchi
6,929,601 B2 8/2005 Nakao
6,932,775 B2 8/2005 Pompei et al.
6,939,039 B2 9/2005 Brunvoll
6,949,069 B2 9/2005 Farkas et al.
6,957,911 B2 10/2005 Wong et al.
6,964,517 B2 11/2005 Welker
6,979,122 B2 12/2005 Yu
6,981,796 B2 1/2006 Hsieh
6,991,368 B2 1/2006 Gerlitz
7,004,623 B2 2/2006 Nakagawa et al.
7,025,500 B2 4/2006 Tabata
7,036,984 B2 5/2006 Penney et al.
7,083,330 B1 8/2006 Yao
7,108,419 B2 9/2006 Harr
7,195,599 B2 3/2007 Carney et al.
7,237,949 B2 7/2007 Lantz et al.
7,255,475 B2 8/2007 Quinn et al.
7,354,194 B2 4/2008 Walker et al.
7,381,189 B2 6/2008 Friedman et al.
7,478,946 B2 1/2009 Harr et al.
2003/0067957 A1 4/2003 Ko et al.
2003/0176809 A1 9/2003 Lin
2005/0002437 A1 1/2005 Fraden
2005/0083991 A1 4/2005 Wong
2005/0226307 A1 10/2005 Lussier et al.
2007/0189358 A1 8/2007 Lane et al.
2007/0253870 A1 11/2007 Weiss et al.
2007/0268956 A1 11/2007 Walker et al.
2008/0175301 A1 7/2008 Chen
2009/0122836 A1* 5/2009 Li ................................ 374/209

FOREIGN PATENT DOCUMENTS

EP 0589212 B1 3/1994
EP 0890829 A1 1/1999
JP 4299225 A 10/1992
JP 10090070 A 2/1994
JP 06160127 A 6/1994
JP 6197869 A 7/1994
JP 06043037 A 4/1998
JP 11037853 A 2/1999
JP 11188008 A 7/1999
JP 2000225095 8/2000
JP 2002051989 A 2/2002

| | | | |
|---|---|---|---|
| JP | 2002214046 | A | 7/2002 |
| WO | 9821556 | A1 | 5/1998 |
| WO | 0052434 | | 9/2000 |
| WO | 2004063686 | A1 | 7/2004 |

OTHER PUBLICATIONS

European Office Action, Application 07009973.4, dated Jan. 11, 2008, 1 page.
Anonymous, “FirstTennp Genius User Guide”, Mar. 2004 , Tyco Healthcare, XP002444529, “the whole document”.
Anonymous, “FirstTemp Genius Infrared Thermometry”, Feb. 2004, Tyco Healthcare, XP002444549, pp. 1-4.
Tyco Healthcare brochure, “Temperature Monitoring”, Jan. 2000, pp. TM-1-TM-8.
Hebbar, Kiran, et al., “Comparison of Temporal Artery Thermometer to Standard Temperature Measurements in Pediatric Intensive Care Unit Patients”, Pediatric Critical Care Medicine, vol. 6, No. 5, Sep. 2005, 5 pages.
Mohammad-Irfan Suleman, et al, “Insufficiency in a New Temporal-Artery Thermometer for Adult and Pediatric Patients”, Anesthesia Analgesia, vol. 95, No. 1, Jan. 2002, 5 pages.
Europeam Search Report regarding related application serial No. EP 09152474.4 dated Sep. 25, 2009, 3 pgs.
European Exam Report regarding related application serial No. EP 07009973.4 dated Oct. 19, 2009, 5 pgs.
European Exam Report regarding related application serial No. EP 09152474.4 dated Oct. 19, 2009, 7 pgs.

* cited by examiner 100
107
301
301
101a
101b
111
101a'
101b'

101
103
105
117
125
127
129
131
141
149
155
157
159
171
173
175
181
211
221
271
273
275
281
283
2A 101
103
105
115
117
119
125
127
129
131
141
149
155
157
159
171
173
175
181
261
5
6
7

281a
281b
275a
275b
271a
271b
273a
127a
273b
127b
281a
281b
101b
281a
159a
157a
159a
281a
101a
221a
221b 155a
155b
211a
211b
213
191a
191b
181a
181b
129a
129b
117b
115b
119b
105a
105b
101a
101b
211b 100
107
325
101a
101b
307
105a
105b
305
303
417
351
301

PROBE COVER CASSETTE WITH IMPROVED PROBE COVER SUPPORT

RELATED APPLICATIONS

This patent application is continuation of U.S. patent application Ser. No. 11/419,438, filed in the United States Patent and Trademark Office on May 19, 2006, which is a continuation in part of U.S. patent application Ser. No. 11/286,620 filed in the United States Patent and Trademark Office on Nov. 23, 2005 (now U.S. Pat. No. 7,354,194), which is a continuation in part of U.S. patent application Ser. No. 10/538,314, filed in the U.S. Patent and Trademark Office on Jun. 13, 2005 (now U.S. Pat. No. 7,237,949), which is the U.S. National Stage application of PCT Application No. PCT/US2003/00224 filed Jan. 6, 2003, the entire contents of which are hereby incorporated by reference herein.

FIELD OF THE INVENTION

The present disclosure generally relates to the field of biomedical thermometers, and more particularly, to probe covers for a tympanic thermometer.

BACKGROUND OF THE INVENTION

Medical thermometers are typically used to facilitate the prevention, diagnosis and treatment of diseases, body ailments, etc. for humans and other animals. Doctors, nurses, parents, and other care providers use thermometers to measure a subject's body temperature. An accurate reading of a subject's core body temperature is needed for effective use and should be taken from the internal or core temperature of a subject's body. Several thermometer devices are known for measuring a subject's body temperature, such as, for example, glass, electronic, and ear (tympanic).

Tympanic thermometers are generally considered by the medical community to be superior for taking a subject's temperature. Tympanic thermometers provide rapid and accurate readings of core temperature, overcoming the disadvantages associated with other types of thermometers. Tympanic thermometers measure temperature by sensing infrared emissions from the tympanic membrane (eardrum) in the external ear canal. The temperature of the tympanic membrane accurately represents the body's core temperature. Further, it only takes a few seconds to measure a subject's temperature in this manner.

Known tympanic thermometers typically include a probe containing a heat sensor such as a thermopile, a pyroelectric heat sensor, etc. See, for example, U.S. Pat. Nos. 6,179,785, 6,186,959, and 5,820,264. These types of heat sensors are particularly sensitive to the eardrum's radiant heat energy. The accuracy with which the sensing probe senses the infrared radiation emitted by the eardrum directly corresponds with the overall accuracy, repeatability and usability of the tympanic thermometer. The sensing probe must be sensitive to the low level of infrared energy emitted by an eardrum while providing a high degree of accuracy, repeatability and thermal noise immunity.

In operation, a tympanic thermometer is prepared for use and a probe cover is mounted onto a sensing probe extending from a distal portion of the thermometer. The probe cover provides a sanitary barrier between the subject and the thermometer. A practitioner or other care provider inserts a portion of the probe having the probe cover mounted thereon into a subject's outer ear canal to sense the infrared emissions from the tympanic membrane. The infrared light emitted from the tympanic membrane passes through a window of the probe cover to the sensing probe. The window is substantially transparent to infrared radiation, thereby allowing infrared radiation from the tympanic membrane to pass through the probe cover to the heat sensing probe of the thermometer. Although an open window would be suitable for taking a temperature measurement, a film (e.g., a plastic film) having a thickness on the order of the wavelength of radiation in the far infrared range typically spans the window to provide a sanitary barrier between the subject and the probe.

The practitioner presses a button to cause the thermometer to take a temperature measurement. The microelectronics process electrical signals from the heat sensor to determine eardrum temperature and render a temperature measurement in a few seconds or less. The probe is removed from the ear canal and the probe cover discarded. A new probe cover is used each time the thermometer is used with a new subject to reduce the risk of cross-contamination (e.g., spreading of pathogens) between subjects.

The thermometer may be used many different times. In a hospital or other health care facility, for example, a thermometer may be used to measure the temperature of up to a few dozen subjects each day. Thus, the care provider needs a supply of probe covers to replace the used probe covers. A plurality of nested probe covers can be supplied to replace used probe covers, for example as shown in U.S. Pat. No. 5,088,834. The probe covers in a nested stack are held together by gravity and/or friction between adjacent probe covers. Nesting probe covers together in this way is efficient use of space, but it has disadvantages. For example, it may be necessary to manually handle the probe covers to separate them for attaching one of the probe covers to a thermometer probe. This is undesirable because it is possible that pathogens or other contaminants could be transferred to the probe covers during the handling. Further, the probe covers (particularly the film portions thereof) are thin and can easily be damaged when handled manually. If the damage results in rips or tears in the film, there is no sanitary barrier between the subject and the thermometer probe. Even if the damaged film is sufficiently intact to provide a barrier, distortions, wrinkling, and/or foreign substances can alter the way infrared radiation is transmitted through the film and can thereby decrease the accuracy of the temperature measurement.

Some of the foregoing problems can be overcome by supplying a plurality of probe covers that are arranged side-by-side. For example, a care provider can carry a cassette comprising a plurality of probe covers releasably attached to a frame. One such cassette is disclosed in U.S. Pat. No. 4,662,360, the disclosure of which is incorporated herein by reference. The probe covers of the cassette (shown in FIGS. 8-10 of the '360 patent) are connected to the frame by two frangible stems. This approach has also been used by the FirstTemp Genius® tympanic thermometer system available from Tyco Healthcare of Mansfield, Mass.

The FirstTemp Genius® system comprises a tympanic thermometer and a holder that releasably holds the thermometer when it is not in use. The holder has a storage compartment for holding a probe cover cassette. The storage compartment has an opening and is configured to hold the cassette so the open ends of the probe covers are accessible through the opening. When the thermometer is received by the holder, the cassette stored in the compartment is underneath the thermometer. Thus, one cassette can be stored in the compartment without interfering with the holder's ability to hold the thermometer. Inside the storage compartment is a base defining a plurality of wells for receiving the releasably attached probe covers. A probe cover can be put on the thermometer probe by inserting the probe into one of the releasably attached probe covers. The force of insertion causes the frangible stems to break, thereby releasing the probe cover from its attachment to the frame before the probe cover is secured to the thermometer probe. The user continues to move the probe in the direction of insertion until a shoulder on the outside of the probe cover contacts the base at the opening to the well. The probe cover is finally attached to the thermometer probe by using the thermometer probe to push the probe cover shoulder against the upward facing part of the base surrounding its well to apply a securement force sufficient to secure the probe cover to the probe. The force required to secure the probe cover to the probe depends on several variables, including friction between the probe and probe cover, the force required (if any) to expand the probe cover to fit on the probe, and the force required (if any) for the probe cover to push one or more probe cover ejectors to retracted positions. As the thermometer probe is inserted into the probe cover, retention bumps on the inside of the probe cover slide past an annular ridge on the thermometer probe. The probe cover is retained on the thermometer probe by engagement of the retention bumps with the annular ridge and by friction between the probe cover and thermometer probe. Once the probe cover is on the probe, the thermometer is ready for use. After a subject's temperature is taken, the probe cover is removed from the thermometer probe and discarded.

In general, it is desirable to make as efficient use of the probe cover storage space in the holder as is practically possible. More efficient use of space could result in a smaller overall size of the thermometer system and/or increase the number of probe covers that can be supplied without restocking probe covers. Moreover, it is also desirable to make use of probe covers with tympanic thermometer systems as user friendly as possible. For example, some probe cover cassettes can be difficult to load in a holder because the releasably attached probe covers can swing out of alignment with the wells in the base of the holder. When this happens, the probe covers have to be manually realigned before they can be received in the wells, which is an inconvenience to the user and also makes it more likely that the probe covers will be contaminated. It is also desirable to provide users tactile and other sensory feedback to facilitate use of probe covers in a tympanic thermometer system.

Accordingly, there is a need for systems and methods for handling a supply of probe covers for use with a tympanic thermometer more efficiently and conveniently.

SUMMARY OF THE INVENTION

In one aspect of the present invention a cassette generally comprises a frame and a plurality of tympanic thermometer probe covers. Each of the probe covers is releasably attached to the frame by at least three frangible connections constructed to allow the respective probe cover to be detached from the frame upon application of a detachment force that breaks the frangible connections. The frangible connections are arranged to support the respective probe cover against pivoting relative to the frame when the probe cover is releasably attached to the frame In yet another aspect of the present invention, a method of securing a probe cover to a probe of a tympanic thermometer generally comprises inserting the probe into an open end of the probe cover while the probe cover is releasably attached to a frame, the frame having a plurality of other probe covers releasably attached thereto. The probe is moved into the probe cover until the probe cover is deformed by application of at least a securement force so as to resiliently bear against the probe for securing itself to the probe while the probe cover remains connected to the frame. The probe continues to be moved into the probe cover with at least a detachment force that detaches the probe cover from the frame. The detachment force is greater than the securement force.

BRIEF DESCRIPTION OF THE DRAWINGS

Corresponding reference numbers designate corresponding parts throughout the drawings.

DETAILED DESCRIPTION

Figure 1:
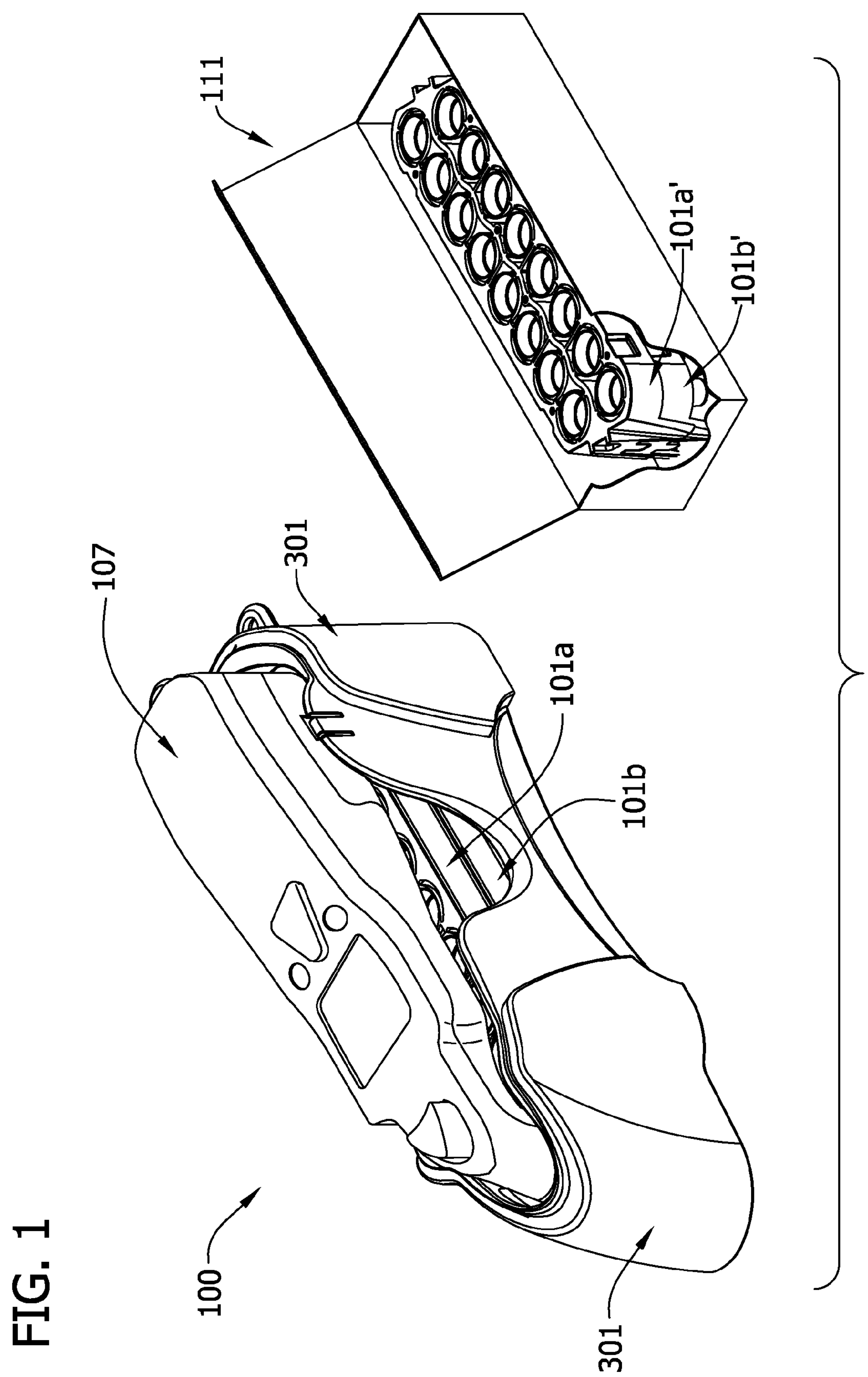
FIG. 1 is a perspective of one embodiment of a tympanic thermometer system of the present invention.

As used herein, the term "proximal" refers to the portion of a structure that is closer to a practitioner in normal use, while the term "distal" will refer to the portion that is further from the practitioner in normal use. As used herein, the term "subject" refers to a human patient or other animal having its body temperature measured. The term "practitioner" refers to a doctor, nurse, parent or other care provider using a tympanic thermometer to measure a subject's body temperature, and may include support personnel. The terms "upper", "lower", "top", "bottom", "side" and other words indicating or suggesting that an object has a particular orientation are used for convenience and are defined in reference to the orientation of the object as shown in the drawings. Those skilled in the art will understand that orientation relative to the up and down directions is not important to operation of the present invention and that different orientations are within the scope of the invention.

Referring now to the drawings, first to FIG. 1 in particular, one embodiment of a tympanic thermometer system is generally designated 100. The thermometer system 100 comprises a tympanic thermometer 107, at least one probe cover cassette 101, and a holder 301 for holding the probe cover cassette(s) and thermometer. The holder 301 of the particular embodiment of the thermometer system 100 shown in FIG. 1 holds first and second stacked probe cover cassettes 101. When referring to a probe cover cassette or an element thereof, the suffix "a" appended to the corresponding reference number indicates reference to an upper cassette stacked on top of a lower cassette and the suffix "b" appended to the corresponding reference number indicates reference to a lower stacked cassette having an upper cassette stacked above it. Thus, in FIG. 1, the upper cassette is generally designated 101*a* and the lower cassette is generally designated 101*b*. It is possible to stack cassettes more than two high, in which case at least one cassette will be an upper and lower cassette at the same time. Accordingly, the terms upper cassette and lower cassette are not absolute and simply identify a cassette in reference to its position relative to another cassette. The thermometer system 100 optionally includes a storage container 111 (e.g., shipping package) for containing at least two probe cover cassettes 101*a*', 101*b*' stacked so at least one probe cover 105*a* of the upper stacked cassette is nested within a probe cover 105*b* of the lower stacked cassette. This disclosure will focus first on the probe cover cassettes 101, and then on the other components of the thermometer system 100.

Figure 2:
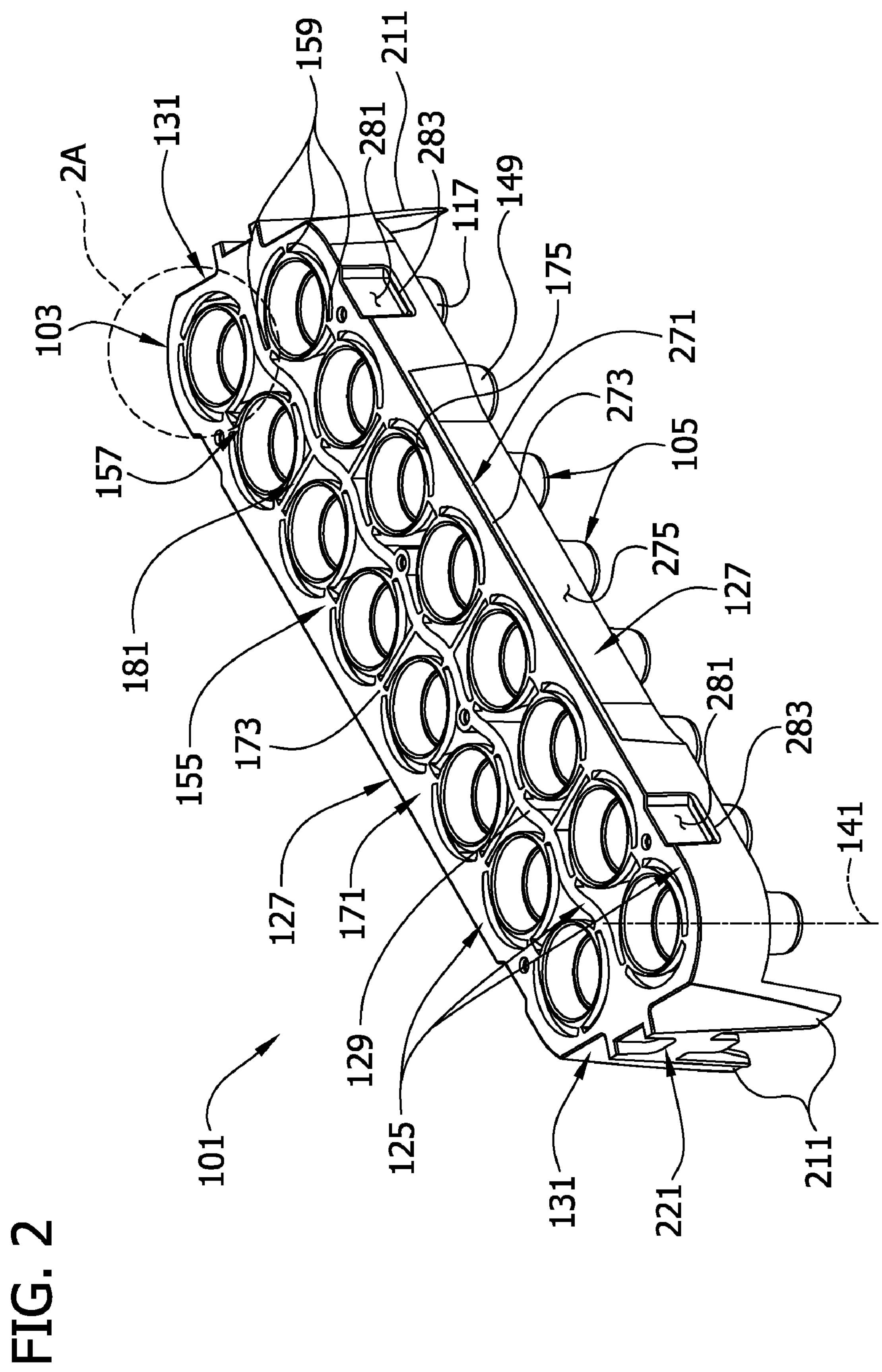
FIG. 2 is a perspective of a probe cover cassette used in the thermometer system of FIG. 1.

FIG. 2 shows a probe cover cassette 101 of the thermometer system 100. The cassette 101 comprises a frame 103 and a plurality of tympanic thermometer probe covers 105 that are releasably attached to the frame. The cassette 101 is constructed to permit the cassette to be stacked with another substantially identical cassette (as shown in FIGS. 3-9) so that the plurality of releasably attached probe covers 105 nest with the probe covers of the other cassette. The probe covers 105 in the embodiment shown in the drawings are described in detail in co-pending and commonly-owned U.S. patent application No. Ser. No. 11/286,620, filed Nov. 23, 2005, the contents of which are hereby incorporated by reference to the extent not inconsistent herewith. Each of the probe covers 105 generally comprises a tubular body 117 having an opening at a proximal end thereof for receiving the probe of a tympanic thermometer 107, and a film-covered infrared-transparent window 119 at distal end thereof for permitting radiation from a subject's tympanic membrane to pass through the window to the probe. The film 115 provides a sanitary barrier between the thermometer probe and the subject. The particular probe covers 105 shown in the drawings are constructed by securing a separately formed film 115 to the distal ends of each of the tubular bodies 117. The film 115 of a probe cover 105 can be constructed from a different material than its body 117. For example, the film 115 can be constructed from a lower density plastic (e.g., low density polyethylene (LDPE)) while the body 117 is constructed from a higher density plastic (e.g., high density polyethylene (HDPE)). However, the film 115 and body 117 of one or more of the probe covers 105 can be constructed of the same material and/or formed integrally together without departing from the scope of the invention The frame 103 is preferably constructed of the same material as the probe cover bodies 117. For example, the probe cover bodies 117 and/or frame 103 may be constructed of a moldable plastic material (e.g., polypropylene, polyethylene, or HDPE). The frame 103 can be manufactured together with the probe cover bodies 117 in an injection molding system. However, the frame 103 and probe cover bodies 117 can be manufactured in any manner and/or constructed of different materials without departing from the scope of the invention. The frame 103 of the embodiment shown in the drawings comprises a plurality of longitudinal supports 125 (See FIG. 2). Two of the longitudinal supports 125 form opposing side walls 127 of the cassette 101. A cassette may include one or more intermediate longitudinal supports (e.g., one or more longitudinal supports 125 located between the side walls 127). The particular cassette 101 shown in the drawings, for example, has a single intermediate support 129. The longitudinal supports 125 are preferably generally parallel and spaced at about equal intervals. For instance, the intermediate longitudinal support 129 of the cassette 101 in the drawings is spaced about midway between the two side walls 127. The longitudinal supports 125 of the illustrated embodiment extend the full length of the cassette 101; however one or more of the longitudinal supports may extend less than the full length of the cassette without departing from the scope of the invention. The frame 103 also comprises two opposing end walls 131 (broadly, end supports) connecting the ends of the longitudinal supports 125. Although the longitudinal supports 125 of the embodiment shown in the drawings form walls, it is understood that the longitudinal supports may be configured in other ways (e.g., as elongate bars) without departing from the scope of the invention.

Figure 3:
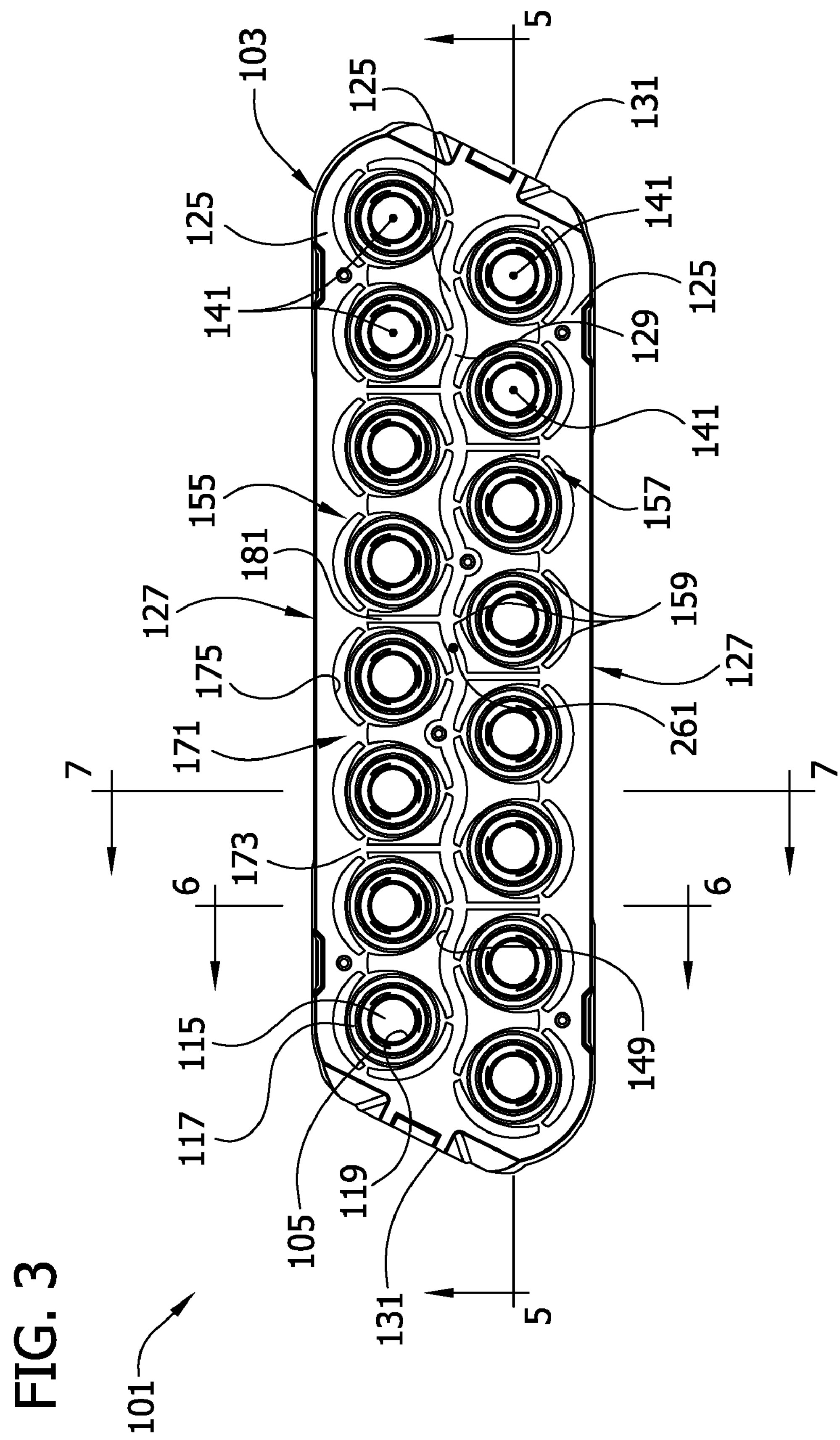
FIG. 3 is a top plan view of the cassette shown in FIG. 2 stacked with another substantially identical probe cover cassette.

The probe covers 105 are preferably arranged in one or more rows and positioned between the longitudinal supports 125. The cassette 101 shown in the drawings has two rows of eight probe covers 105. The rows are separated by the intermediate support 129. Thus, the cassette 101 comprises a supply of sixteen probe covers 105. Increasing or decreasing the number of intermediate supports facilitates arrangement of the probe covers 105 in different numbers of rows. In general, it is desirable to design a cassette so the probe covers 105 thereof are arranged as closely as is practically possible to make the most efficient use of space. In some cases (e.g., when the probe covers are at least partly rounded on the outside) it is possible to decrease spacing between adjacent rows by offsetting the probe covers in one row with respect to the probe covers in the adjacent row, as is shown in FIG. 3. For example, the longitudinal axes 141 of the probe covers 105 in one row are aligned with points (e.g., the midpoints) between two probe covers in an adjacent row. Further, the intermediate support 129 turns back and forth between the offset probe covers 105 of the two adjacent rows and thereby forms a plurality of concave surfaces 149. The probe covers 105 are positioned adjacent the concave surfaces 149, allowing the overall spacing between the rows to be reduced. Reducing the spacing between adjacent rows allows the overall width of the cassette 101 to be reduced without reducing the number of rows or the size of the probe covers 105.

Figure 2A:
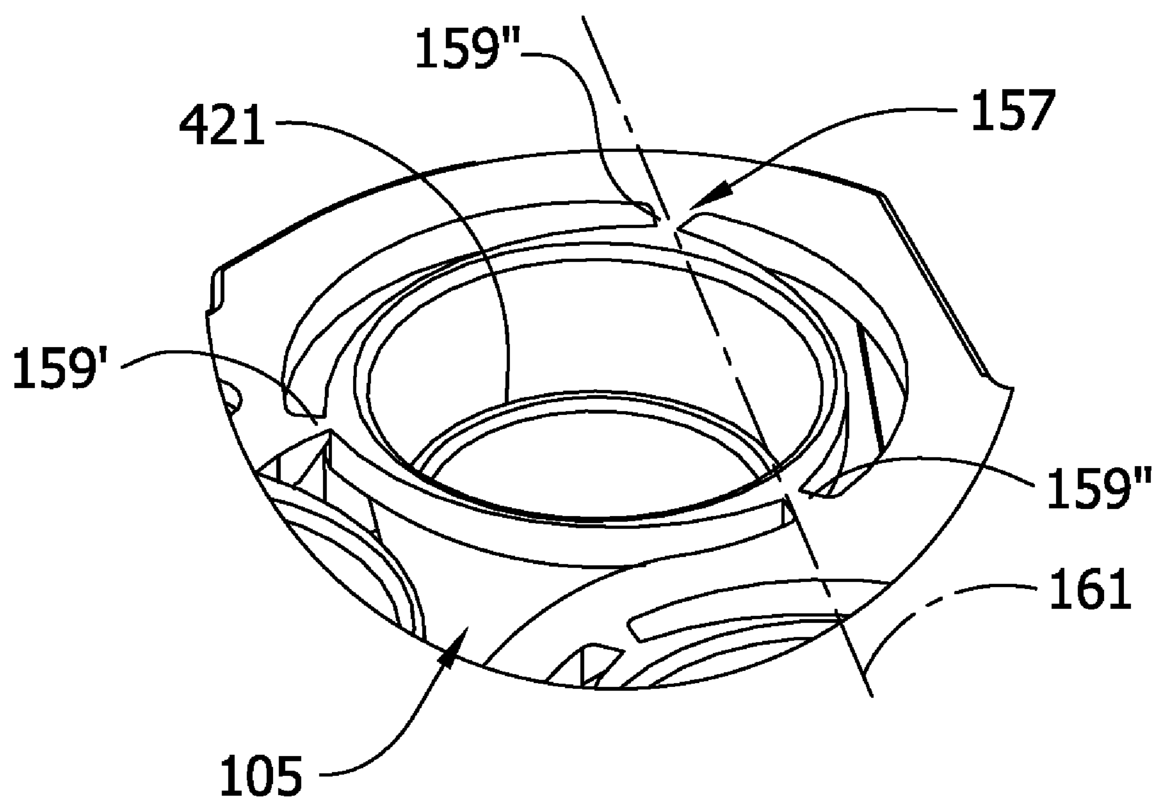
FIG. 2A is an enlarged fragmentary view thereof.

The longitudinal supports 125 and end walls 131 of the cassette 101 extend down from the upper surface 155 of the cassette, which is preferably contained substantially within a horizontal plane. Each of the probe covers 105 is releasably attached to the cassette 101 at the upper surface 155 of the cassette by a frangible connection 157 to the frame 103. The frangible connection 157 is constructed to allow the probe cover 105 to be detached from the frame 103 upon application of a detachment force. However, the frangible connection 157 is constructed to support the probe cover 105 against pivoting relative to the frame 103 while the probe cover is still attached to the frame. As shown in the drawings and in particular FIG. 2A), the frangible connection 157 preferably comprises three frangible stems 159 spaced generally equidistantly around the perimeter of the respective probe cover 105 and connecting the probe cover to the frame 103. The frangible stems 159 are preferably positioned so at least one frangible stem 159' is spaced away from an imaginary line 161 containing the remaining frangible stems 159". This avoids the possibility that all of the frangible stems 159 connecting one of the probe covers 105 to the frame 103 are contained substantially a single line, which in combination with the relatively low rigidity of the frangible stems can permit the respective probe cover 105 to pivot on that line relative to the frame 103. It will be understood that a frangible connection between the frame and a probe cover may have more or less than three frangible stems without departing from the scope of the present invention. It is also understood that other types of frangible connections (e.g., a frangible connection formed by a ring gate of an injection molding apparatus) may support one or more probe covers 105 against pivotal movement relative to the frame 103. The detachment force required to detach a probe cover 105 from the frame 103 is preferably greater than a securement force required to secure the probe cover to the thermometer 107, for reasons that will be explained below.

The frame 103 includes reinforcing structures that counter the tendency of the frame to deform upon application of the detachment force to one of the probe covers 105. For example, a web 171 extends laterally along the upper surface 155 of the cassette 101 from each of the side walls 127 toward the adjacent row of probe covers and lengthwise between the end walls 131 of the cassette. The webs 171 are shaped to form a plurality of spurs 173 extending laterally into the spaces between adjacent probe covers 105. Each spur 173 supports two frangible stems 159, one connecting the spur to each of the two adjacent probe covers 105 (see FIG. 2). One of the functions of the spurs 173 is to facilitate spacing the frangible stems 159 so they are spaced substantially equidistant around the circumferences of the probe covers 105. For instance, the spurs 173 facilitate connection of the frangible stems 159 to the probe covers 105 at locations that are remote from the side walls 127. The greatest lateral extent of the webs 171 away from the side walls of the cassette 101 is at the spurs 173. Between the spurs 173, the web 171 is configured to form a concave edge surface 175 generally matching the contours of the perimeter of the probe cover 105. The web 171 stiffens the side walls 127, and thereby stiffens the frame 103.

Figure 6:
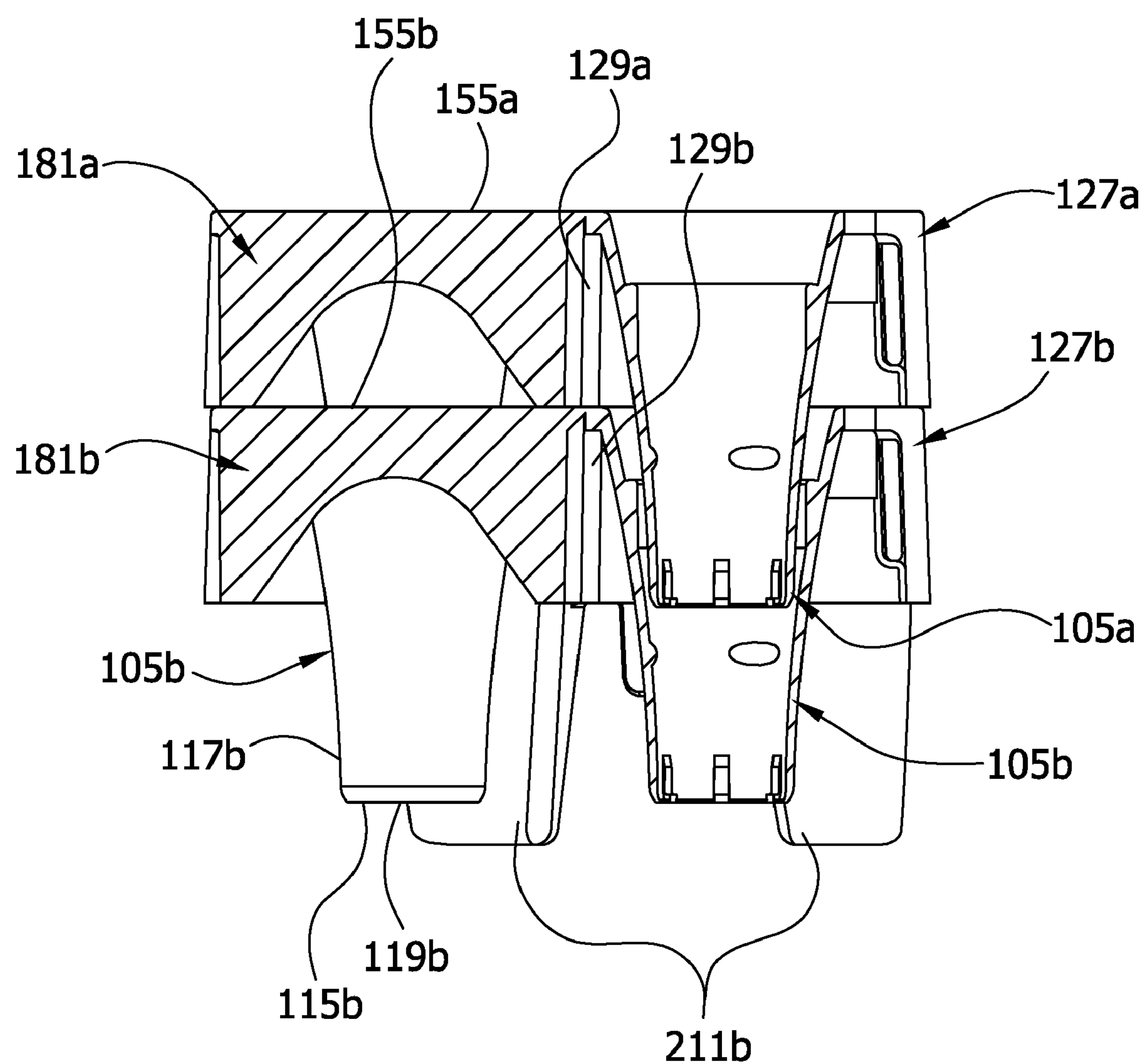
FIG. 6 is a section of the stacked cassettes taken in the plane including line 6-6 of FIG. 3.
Figure 7:
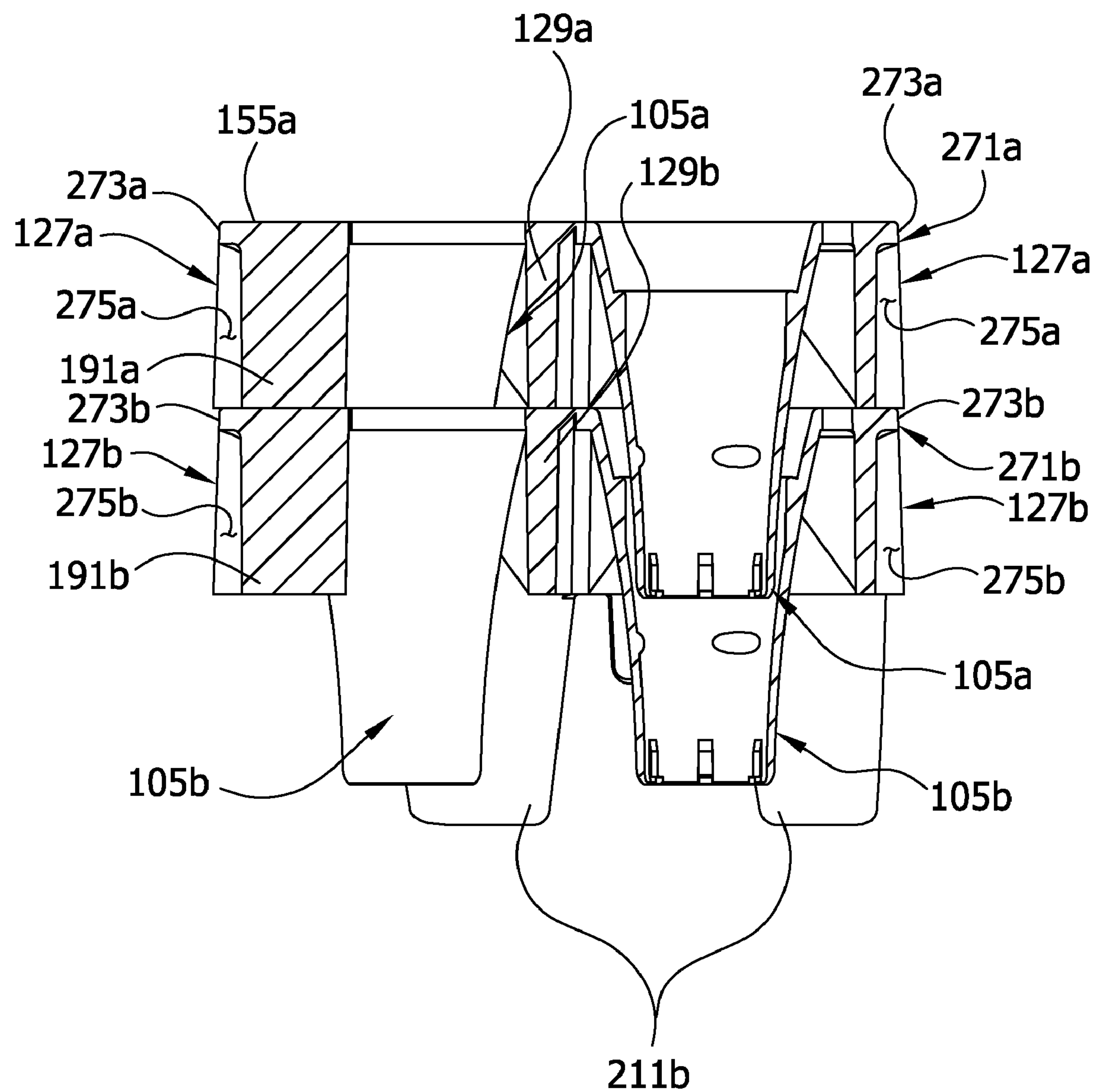
FIG. 7 is a section of the stacked cassettes taken in the plane including line 7-7 of FIG. 3.

The frame 103 also comprises a plurality of cross braces 181 extending between adjacent probe covers 105 in a row and connecting the longitudinal supports 125 at various locations between the end walls 131 of the cassette 101. The cross braces 181 also help limit twisting and/or deflection of the frame 103, including localized twisting and/or deflection of the frame while the detachment force is being applied to an adjacent probe cover 105. The cross braces 181 shown in the drawings have the form of a wall extending from one longitudinal support 125 (e.g., from the side walls 127 at a location coinciding with a spur 173 to the intermediate support 129). The cross braces 181 may have an arch shape, as shown in FIG. 6. The arched configuration of the cross braces 181 reduces the amount of material needed to make the cross braces as compared to cross braces that are configured as a rectangular wall. Cross braces may have other shapes without departing from the scope of the invention. A cross brace can be positioned between each probe cover and its two neighbors in the same row. This would result in each probe cover being adjacent two longitudinal supports and either two cross braces or a cross brace and an end wall. However, it is not necessary to position a cross brace between each and every probe cover in a row. In the embodiment shown in the drawings, for example, a cross brace 181 is positioned between each probe cover 105 and only one of its two neighbors in its row. Each row of the cassette 101 in the drawings alternates between having a cross brace 181 between adjacent probe covers 105 in that row and having no cross brace between adjacent probe covers in that row. Consequently, each of the probe covers 105 is adjacent two of the longitudinal supports 125 and at least one cross brace 181 or an end wall 131 of the cassette 101. Even fewer cross braces can be used without departing from the scope of the invention.

Figure 9:
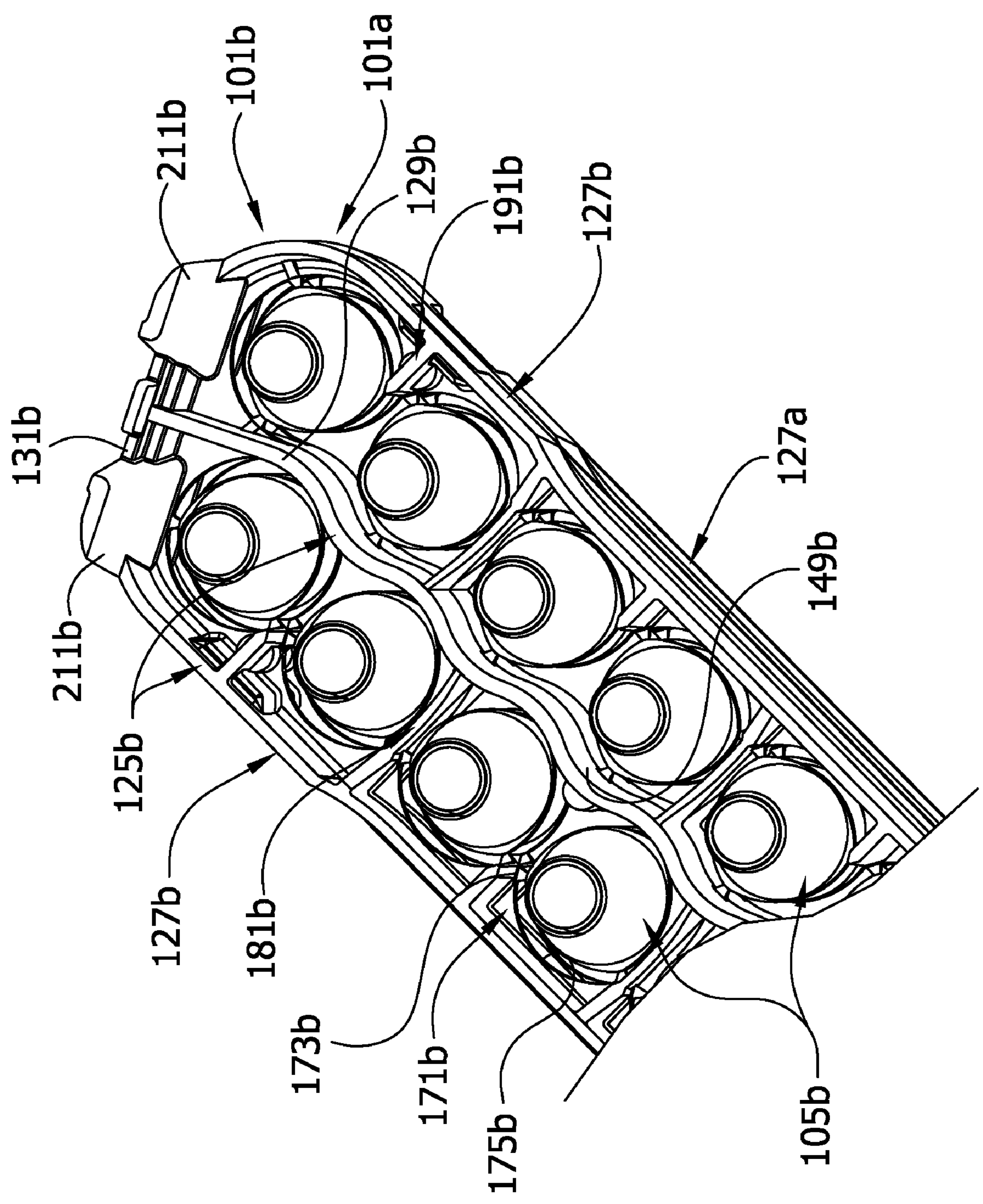
FIG. 9 is a fragmentary perspective of a portion of the stacked cassettes from a vantage point beneath the stacked cassettes.

The frame 103 still further comprises a plurality of flanges 191 extending horizontally from the longitudinal supports 125 (e.g., from the side walls 127). The flanges 191 are similar to the cross braces 181, except that they do not extend all the way from the side wall 127 to the intermediate support 129, and are preferably rectangular in shape. The flange 191 shown in FIG. 7, for example, comprises a generally rectangular wall extending generally perpendicularly inward from one of the side walls 127 (e.g., at a location coinciding with one of the spurs 173). Each spur 173 of the cassette 101 shown in the drawings is supported by either a cross brace 181 or a flange 191. Like the cross braces 181, the flanges 191 help the frame 103 resist twisting and/or deflection, including localized twisting and/or deflection of the frame while an adjacent probe cover 105 is being detached from the frame. As best seen in FIG. 9, the cassette 101 shown in the drawings comprises a plurality of flanges 191 extending from each of the side walls 127 at intervals coinciding with gaps between the cross braces 181. Consequently, each of the side walls 127 comprises an alternating series of cross braces 181 and flanges 191 for stiffness reinforcement. A greater or lesser number of flanges than is shown in the illustrated embodiment can be used without departing from the scope of the invention.

The intersections between the cross braces 181 with the respective side walls 127 and web 171 as well as the intersections between the flanges 191 and the respective side walls and web each are defined by three intersecting walls. Because the three walls (i.e., the side wall 127, the laterally extending web 171 and the cross brace 181 or flange 191) at the intersections are oriented in three different planes, the intersections provide additional resistance to twisting and/or deflection of the frame 103. Preferably, the three walls meeting at each of the intersections are in substantially mutually orthogonal relation to one another at the intersections as shown in FIG. 9. The various reinforcing features of the frame 103 (including the longitudinal supports 125, webs 171, cross braces 181, flanges 191, and the arrangement thereof in which three walls intersect at a plurality of locations on the frame) in combination make the frame much stiffer than the frames of the prior art probe cover cassettes. This additional stiffness is advantageous because it alleviates the need to decide between providing external support for the frame 103 while a detachment force is being applied to one of the probe covers 105 or accommodating substantial twisting and/or deflection of the frame when a probe cover is being detached therefrom.

Figure 4:
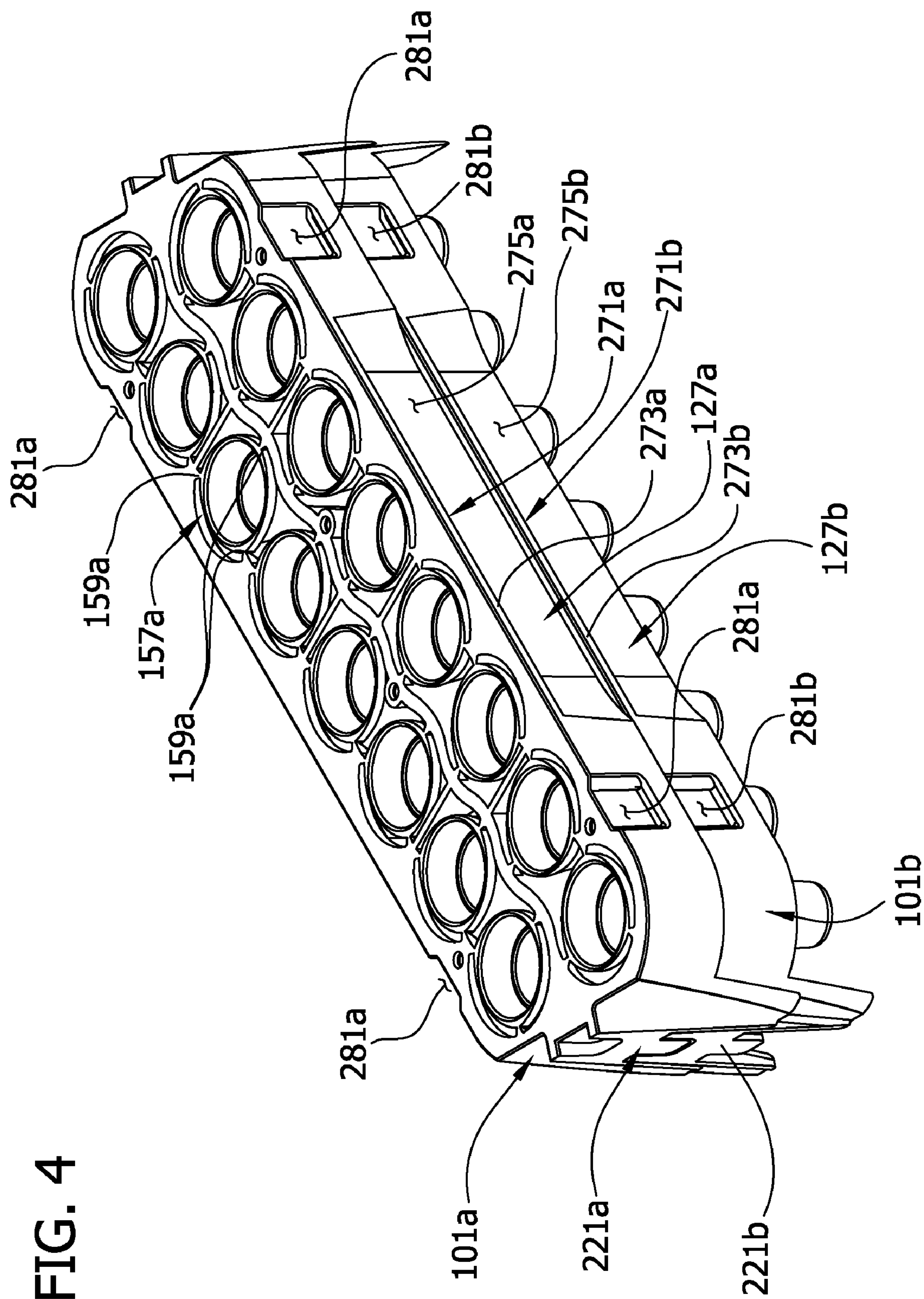
FIG. 4 is a perspective of the stacked cassettes shown in FIG. 3.
Figure 5:
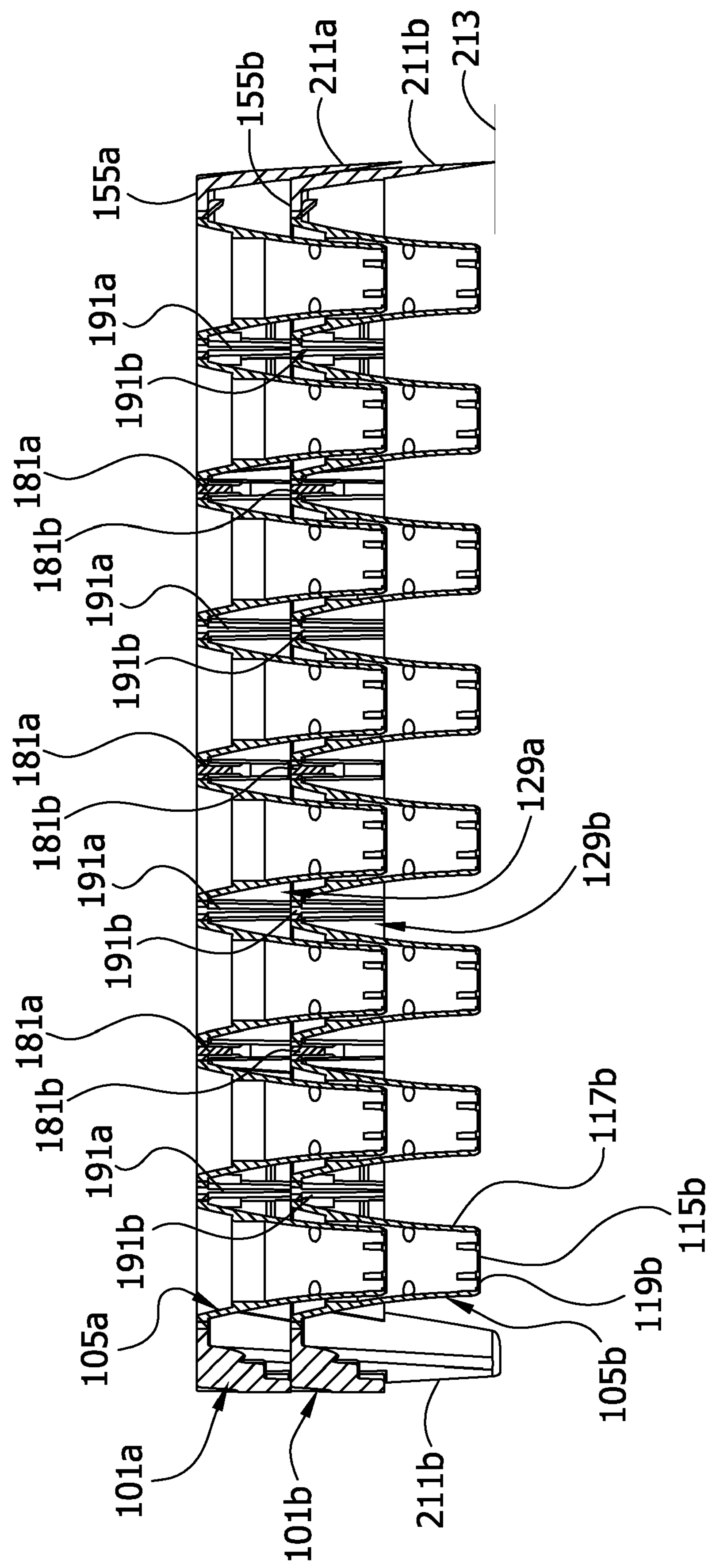
FIG. 5 is a section of the stacked cassettes taken in the plane including line 5-5 of FIG. 3.

The frame 103 also has plurality of legs 211 (e.g., four legs) disposed to engage a generally flat surface 213 and hold the probe covers 105 spaced away from that surface, as shown in FIG. 5. Holding the probe covers 105 spaced away from the surface 213 helps protect the probe covers, in particular the film 115, from damage and/or contamination from the surface (e.g., when the cassette is placed on a work surface). The legs 211 are shaped and arranged to receive a frame of a substantially identical cassette when stacked therewith. For example, the legs 211 of the cassette 101 shown in the drawings angle generally outward. This allows the legs 211*a* of a substantially identical cassette 101*a* stacked on top of a lower cassette 101*b* to overlay the legs 211*b* of the lower cassette, as best seen in FIG. 4.

Figure 8:
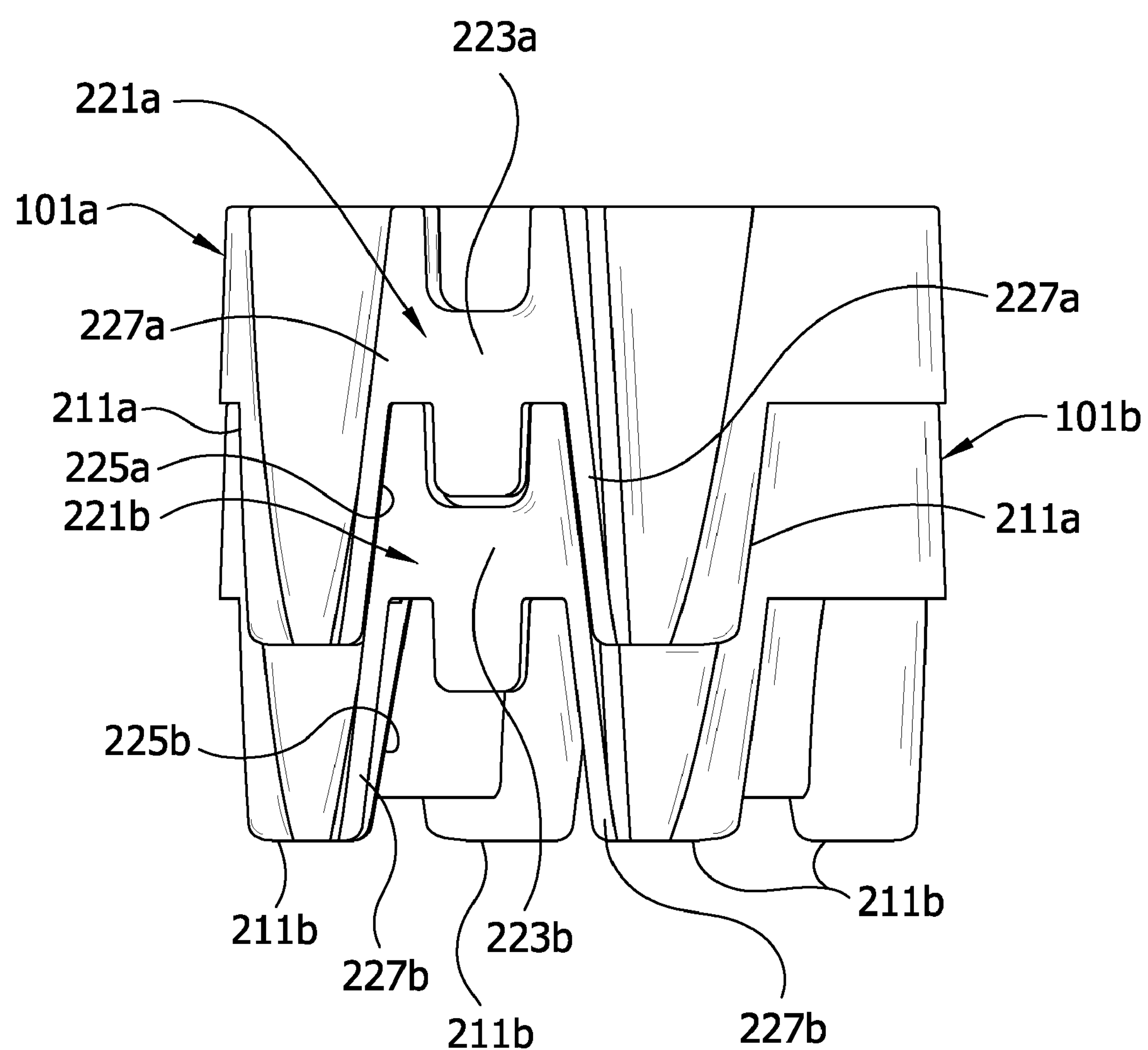
FIG. 8 is an end view of the stacked cassettes shown in FIGS. 3-7.
Figure 8A:
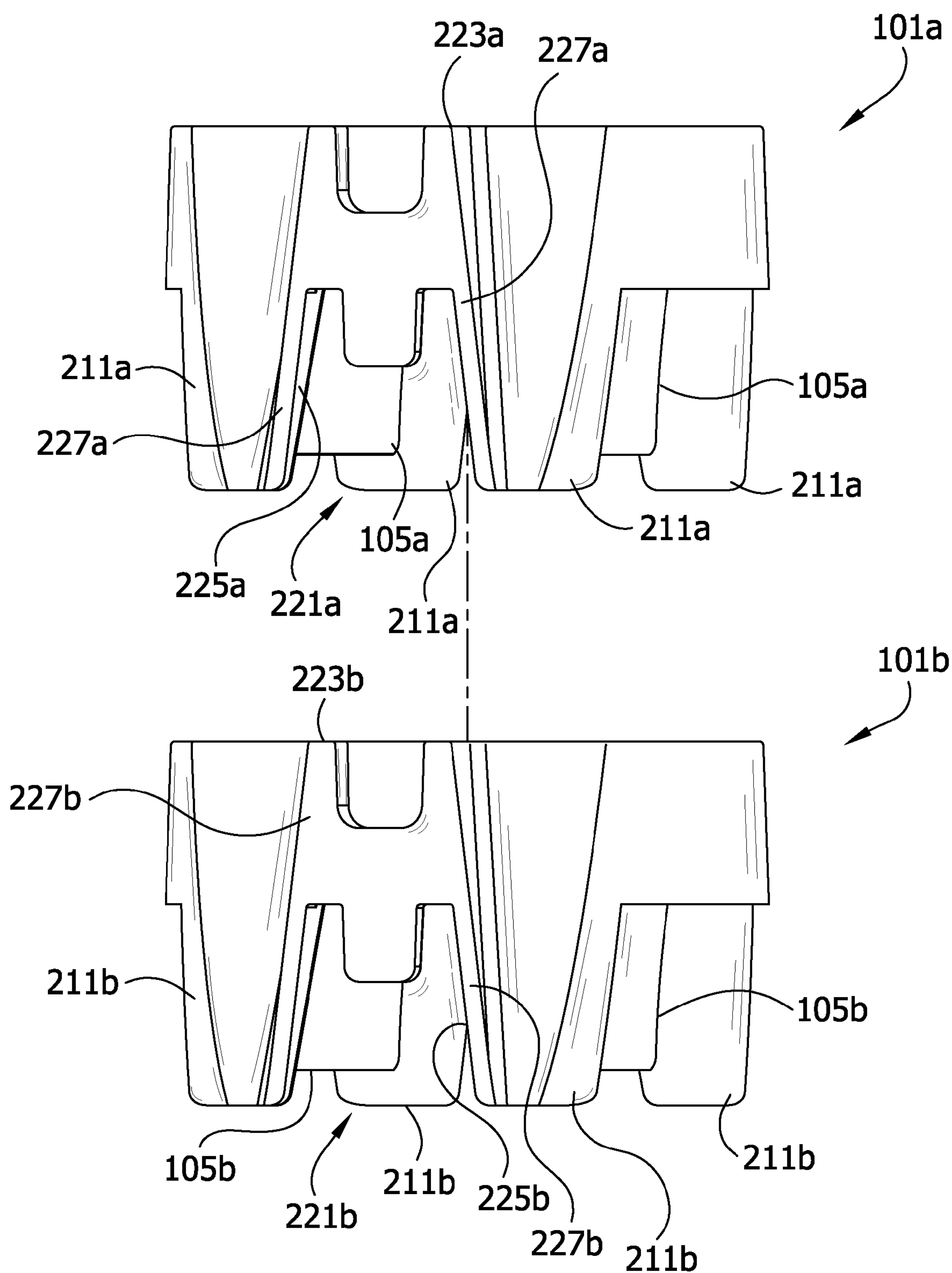
FIG. 8A is an end view similar to FIG. 8, but with the cassettes shown apart in preparation of stacking.

The frame 103 also comprises a cassette aligning system 221 that facilitates bringing a substantially identical cassette into substantial alignment with and/or into a substantially similar orientation as the cassette 101 during stacking. As shown in FIGS. 8 and 8A, in one embodiment the cassette aligning system 221 comprises at least one tapered guide wedge 223 and at least one tapered notch 225 in the frame 103 (e.g., on one of the sides or ends of the cassette). The wedge 223 includes a pair of walls 227 that are located generally between the legs 211 and are spaced apart laterally of each other. The walls 227 diverge from each other from the top of the cassette 101 to the bottom of the cassette. The notch 225 is defined on its laterally opposite sides by lower portions of the walls 227 of the wedge 223, and generally tapers from a greater width at an open end at the bottom of the cassette 101 to a lesser width at an upper end of the notch. The upper end of the notch 225 can be closed as shown in the drawings or open. When the upper cassette 101*a* is lowered onto the lower cassette 101*b* for stacking (e.g., from the position shown in FIG. 8A), the notch 225*a* of the upper cassette 101*a* receives the upper ends of the walls 227*b* of the guide wedge 223*b* of the lower cassette 101*b*. As the upper cassette 101*a* moves further downward on the lower cassette 101*b*, the interior surfaces of the walls 227*a* of the guide wedge 223*a* of the upper cassette engage exterior surfaces of the walls 227*b* of the guide wedge 223*b* of the lower cassette 101*b*. This engagement results in lateral alignment of the upper and lower cassettes 101*a*, 101*b* as they are stacked. The engagement of the legs 211*a*, 211*b* on opposite longitudinal ends of the cassettes 101*a*, 101*b* produces longitudinal alignment of the stacked cassettes. It will be appreciated that because the legs 211*a*, 211*b* flare outwardly in a longitudinal direction away from the ends of the cassettes 101*a*, 101*b* toward the bottom of the legs, that the cassettes are initially easy to mate upon stacking. The lower ends of the legs 211*a* of the upper cassette 101*a* are spread apart more widely than the upper ends of the legs 211*b* of the lower cassette 101*b*. However, as the cassettes 101*a*, 101*b* move closer together, the legs 211*a*, 211*b* engage and more precisely align the cassettes.

The frame 103 is preferably configured to maintain a minimum spacing between nested probe covers 105*a*, 105*b* of stacked cassettes 101*a*, 101*b*. In the embodiment shown in the drawings, for example, the upper cassette 101*a* has longitudinal supports 125, flanges 191, and downward facing surfaces at the narrow end of the notches 225 of the cassette aligning system 221 that are configured to engage the frame 103*b* of the lower cassette 101*b* and maintain spatial separation between the probe covers 105*a*, 105*b* of the upper cassette and lower cassette 101*b*. The contact between the frames 103*a*, 103*b* of the upper and lower cassettes 101*a*, 101*b* is distributed over a large portion of the cassettes. For instance, the contact between the frames 103*a*, 103*b* of the embodiment shown in the drawings is distributed along the longitudinal supports 125 (e.g., the side walls 127 and intermediate/central support 129), flanges 191, and the alignment systems 221 on the end walls 131. This distribution of the contact between the upper and lower cassettes 101*a*, 101*b* is advantageous because rather than being concentrated in a relatively small part of the frame 103, which would decrease the amount of force required to cause failure, the force required to maintain separation between the probe covers 103 (e.g., while one of the probe covers is being detached from a stacked cassette 101) is distributed more evenly throughout the frame. There are many other ways to configure a frame of a cassette so that it engages a frame of another cassette to maintain spatial separation of nested probe covers without departing from the invention, including using different combinations of one or more elements of the frame shown in the drawings and/or different frame elements other than the elements shown in the drawings (e.g., a separate spacer, not shown) to maintain spatial separation between nested probe covers.

The cassette 101 is also designed so that it can be stacked with another substantially identical cassette in either of two different orientations. For instance, the cassette 101 shown in the drawings has radial symmetry about an axis 261 (FIG. 3) parallel to the longitudinal axes 141 of the probe covers 105. Accordingly, if the cassette 101 has an orientation relative to another cassette that permits stacking of the two cassettes, the cassette will also have an orientation relative to the other cassette that permits stacking of the cassettes when the cassette is rotated on the axis 261 through an angle of about 180 degrees. In the embodiment shown in the drawings, for example, the upper cassette 101*a* can be stacked with the lower cassette 101*b* in either of two orientations that are about 180 degrees apart. This makes handling the cassette 101 more convenient because a user is not required to rotate the cassette more than ninety degrees on the axis 261 to bring the cassette into one of the orientations suitable for stacking the cassette with another substantially identical cassette.

The cassette 101 further comprises a grip 271 (See FIG. 4) for separating the cassette from other cassettes in a stack of cassettes. In general, the grip 271 is a feature of the cassette 101 that allows a practitioner to feel the boundary(ies) between two or more stacked cassettes and then grip the desired number of cassettes to separate them from the rest of the stack. For example, the grip 271 may comprise one or more ridges 273 on the sides of the frame 103, as shown in FIG. 4. In the particular cassette 101 shown in the drawings, portions of the side walls 127 extending down from adjacent the upper surface 155 of the cassette under the ridges 273 define recessed areas 275. Consequently, the ridges 273 extend laterally outward above the recessed areas 275 of the side walls. When a substantially identical upper cassette 101*a* is stacked on top of the lower cassette 101*b*, the ridges 273*b* of the lower cassette extend laterally from below the recessed areas 275*a* of the side walls 127 of the upper cassette 101*a*, allowing the practitioner to run one or more fingers along either the side of the cassette to feel the ridge and identify the boundary between stacked cassettes. Likewise the practitioner can hold one or more ridges 273*a* of the upper cassette 101*a* with one hand and hold one or more ridges 273*b* of the lower cassette 101*b* with the other hand to facilitate pulling the cassettes apart. Laterally projecting ridges can extend outward from the side walls to form grips without any recesses being associated therewith in the scope of the invention. However, using recessed areas 275 of the side walls 127 to define the ridges 273 for the grips 271 allows the grips to be formed without increasing the overall width of the cassette 101.

The cassette 101 also comprises one or more detent receptacles 281 for releasably receiving a detent from a retaining mechanism in a holder. A lip 283 (FIG. 2) is defined by the lower end of the receptacle 281. In the embodiment shown in the drawings, there are a total of four such receptacles 281, each of which defines a lip 283. Two of the receptacles 281 are on each of the side walls 127, one to the right and one to the left of the recessed areas 275 of the side walls under the grip 271. These receptacles 281 and lips 283 can be used to snap the cassette into a holder, as will be described hereinafter.

FIGS. 3-9 show one embodiment of a combination of upper and lower stacked cassettes 101*a*, 101*b* according to the present invention. The probe covers 105*a* of the upper cassette 101*a* are nested with aligned probe covers 105*b* of the lower cassette 101*b*. The guide wedges 223*b* of the cassette aligning systems 221*b* of the lower cassette 101*b* are received in the corresponding notches 225*a* of the cassette aligning system 221*a* of the upper cassette 101*a*. The frame 103*a* of the upper cassette 101*a* is in contact with the frame 103*b* of the lower cassette 101*b*, thereby holding the probe covers 105*a* of the upper cassette spaced away from the probe covers 105*b* of the lower cassette. As shown in FIGS. 5-8, for example, the upper cassette's 101*a* longitudinal supports 125*a*, including the two side walls 127*a* and the intermediate support 129*a*, the flanges 191*a*, and the downward facing surfaces of the aligning system 221*a* engage the frame 103*b* of the lower cassette 101*b* and prevent further movement of the upper cassette toward the lower cassette. It is apparent from the two stacked cassettes 101*a*, 101*b* that any number of cassettes can be stacked together in this manner to form a single stack.

Figure 10:
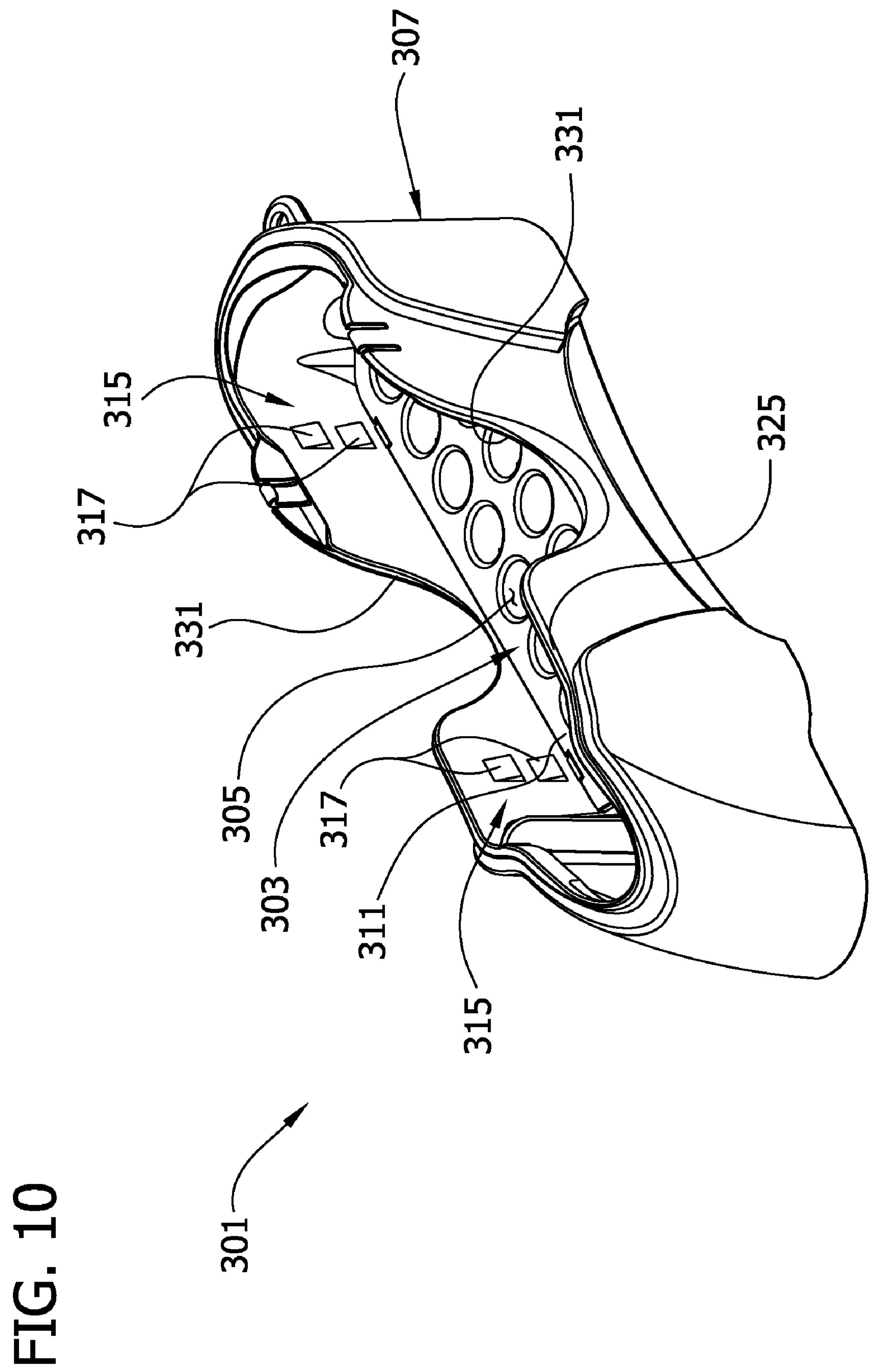
FIG. 10 is a perspective of a holder of the tympanic thermometer system.

FIG. 10 shows one embodiment of a holder 301 that may be used to hold one or more cassettes 101. The holder 301 comprises a base 303 defining a plurality of wells 305 for receiving at least the distal ends of the probe covers 105 and a housing 307 at least partially enclosing the base 303. For example, the holder 301 may be used to hold the two stacked cassettes 101*a*, 101*b* (as shown in FIGS. 11-15) so at least the distal ends of the probe covers 105*b* of the lower stacked cassette are received in the wells 305. The base 303 comprises an upper surface 311 similar to the upper surface 155 of the cassette 101. As shown in FIG. 10, for example, the upper surface 311 of the base is engaged by the frame 103*b* of the lower cassette 101*b* in a manner similar to the way the upper surface 155*b* of the lower cassette is engaged by the frame 103*a* of the upper cassette 101*a*. When the probe covers 105*b* of the lower cassette 101*b* are placed in the wells 305, the side walls 127*b* and intermediate support 129*b* of the lower cassette engage the upper surface 311 of the base 303 and hold the probe covers 105*b* spaced above the bottoms of the wells. Contact between the upper surface 311 of the base 303 and the frame 103*b* of the lower cassette 101*b* is also analogous to the contact between the upper cassette 101*a* and the lower cassette in that it is widely distributed over the cassette so the force applied to the lower cassette 101*b* by the base 303 (e.g., to prevent the lower cassette 101*b* from deflecting in a direction toward the base while a probe cover 105*b* is being detached) is not concentrated in a particular portion of the cassette.

The holder 301 also has a cassette retaining system 315 (FIG. 10) operable to hold one or more cassettes 101 in the holder. The retaining system 315 comprises eight detents 317 positioned to be received in a corresponding one of the detent receptacles 281*a*, 281*b* in the frames 103*a*, 103*b* of the upper and lower cassettes 101*a*, 101*b*. It is understood that any number of detents (including only one detent) may be used within the scope of the invention. The holder 301 shown in the drawings is designed to hold two stacked cassettes 101*a*, 101*b*. When used to hold two stacked cassettes 101*a*, 101*b* it is preferable for the retaining system 315 to comprise at least one detent 317*b* positioned to be received in one of the detent receptacles 281*b* in the lower stacked cassette 101*b* and at least one detent 317*a* positioned to be received in one of the detent receptacles 281*a* in the upper stacked cassette 101*a*. Still more preferably, the retaining system 315 comprises a plurality of detents 317*b* positioned to be received in corresponding receptacles 281*b* of the lower stacked cassette 101*b* and a plurality of detents 317*a* positioned to be received in corresponding receptacles 281*a* of the upper stacked cassette 101*a*. For example, the holder shown in the drawings has eight detents 317 on the inside of the housing 307 and positioned so four of the detents 317*b* can be received in the four receptacles 281*b* of the lower stacked cassette 101*b* and the remaining four detents 317*a* are received in the four receptacles 281*a* of the upper stacked cassette 101*a*. Each of the detents 317*a*, 317*b* and/or the frames 103*a*, 103*b* of the cassettes 101*a*, 101*b* are constructed to deform when the cassettes are loaded in the holder 301 to permit the lips 283*a*, 283*b* on the side walls 127*a*, 127*b* of the cassettes to slide past the detent(s) to snap the cassette into the holder.

Figure 11:
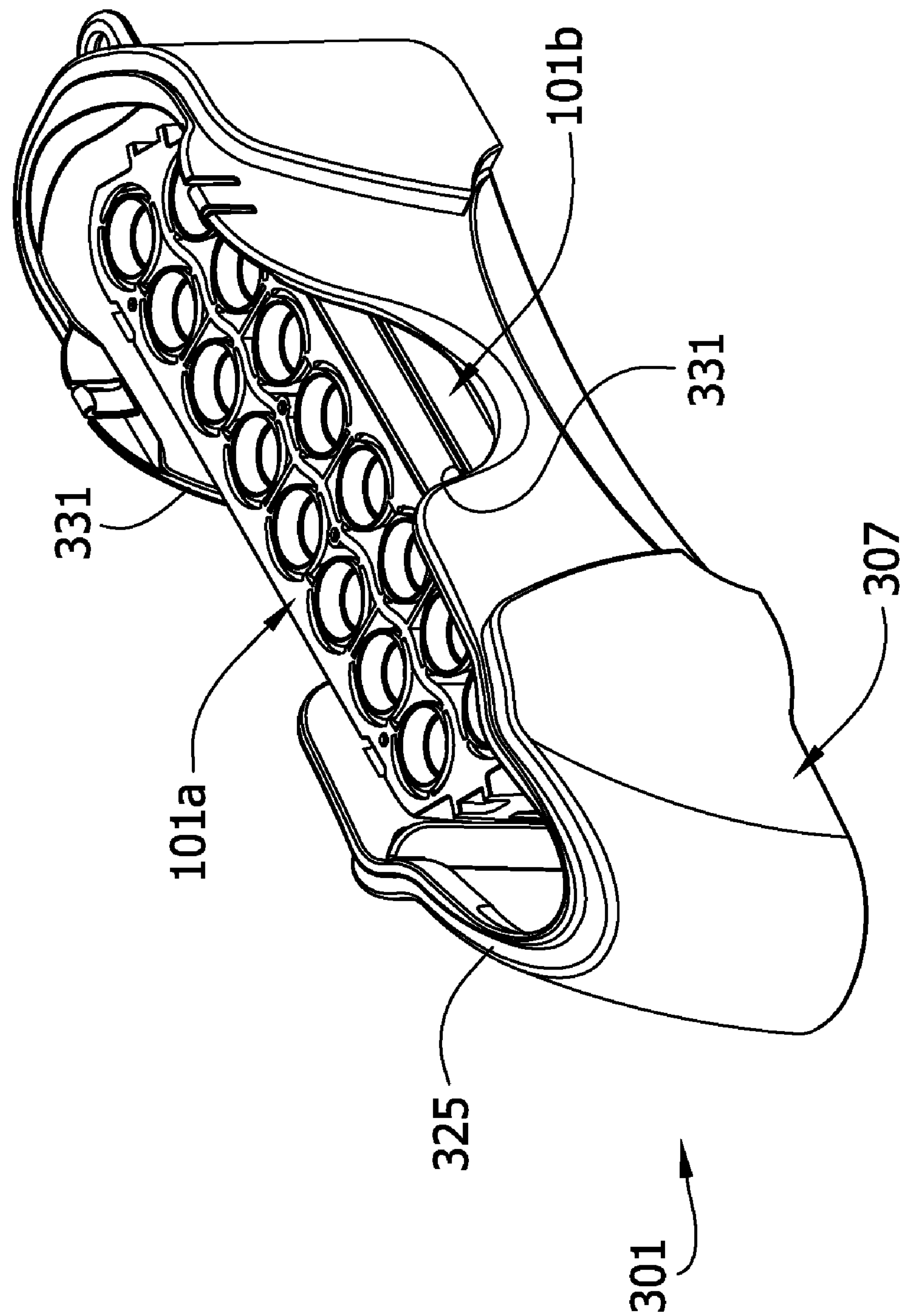
FIG. 11 is a perspective of the holder and two stacked cassettes therein.
Figure 12:
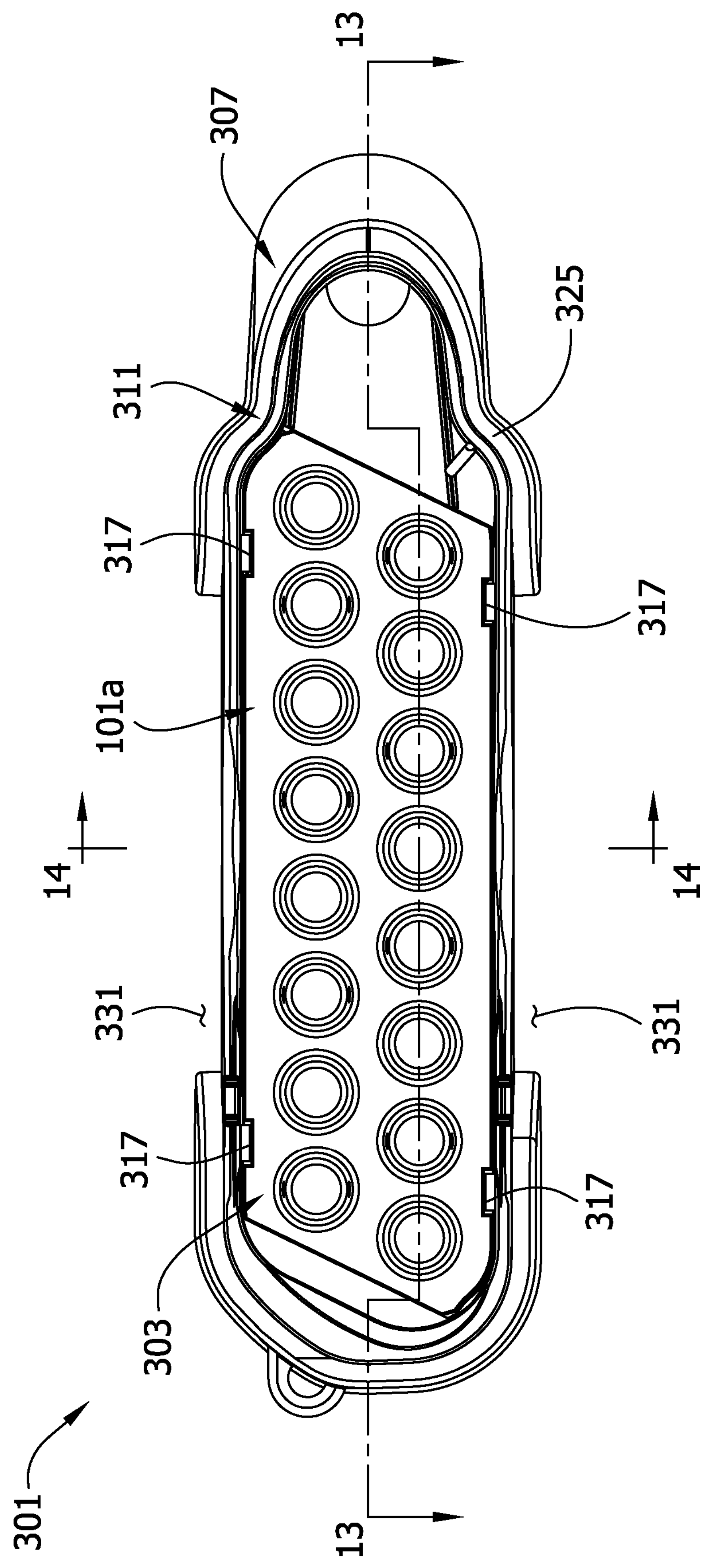
FIG. 12 is a top plan view thereof.
Figure 13:
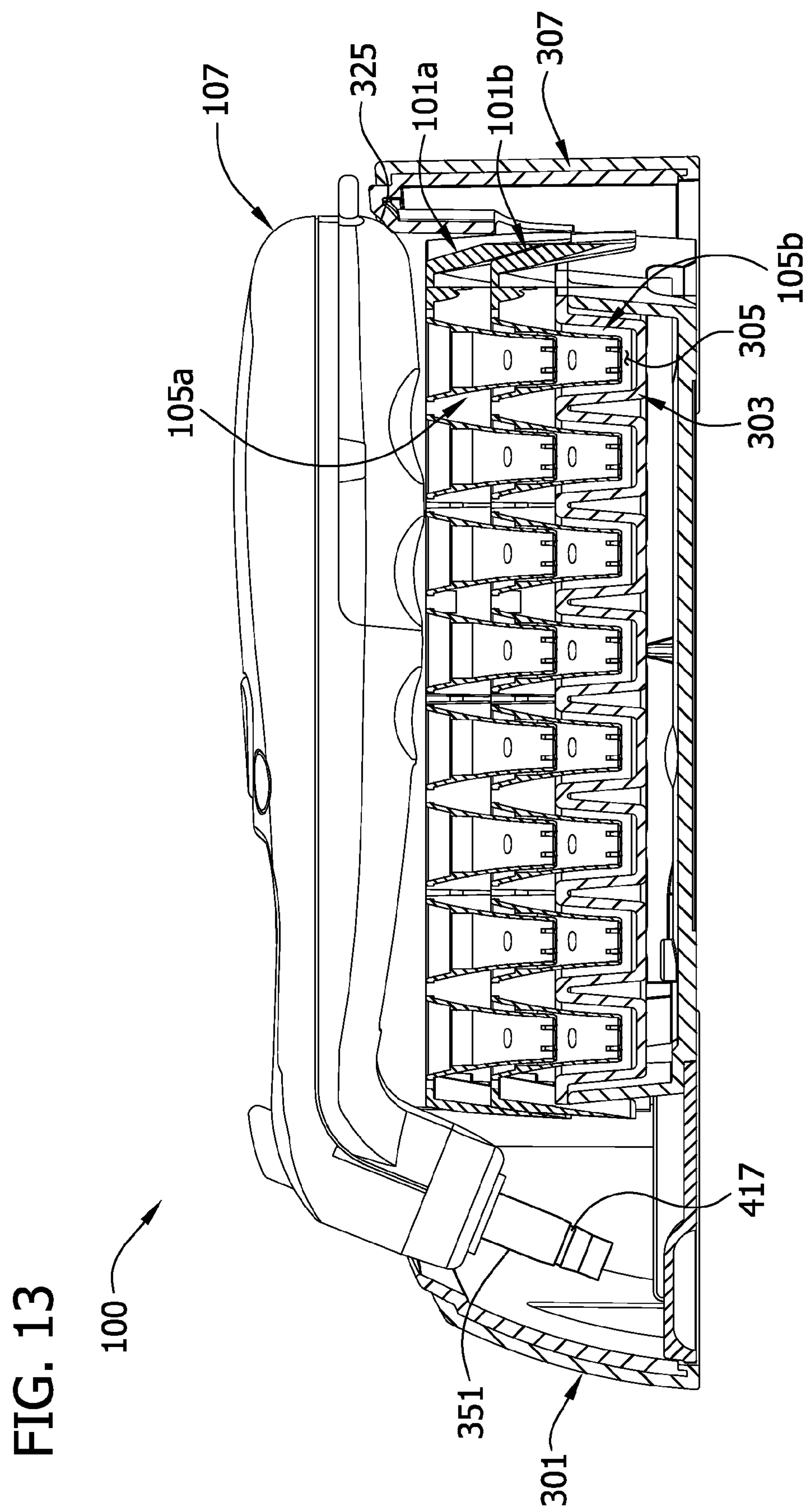
FIG. 13 is a section of the thermometer system taken as indicated by line 13-13 of FIG. 12 and further illustrating the thermometer held in the holder.

The housing 307 is configured to extend somewhat above the upper surface 155*a* of the upper cassette 101*a* but may extend only to a location somewhat below the upper surface of the upper cassette or to a location that is even therewith in the scope of the invention. For example, the housing 307 may extend a short distance above the upper surface 155*a* of the upper stacked cassette 101*a*. This upper end 325 of the housing 307 forms a cradle for receiving a tympanic thermometer 107 as shown in FIG. 13. Thus, in contrast to the prior art holders, it is possible to store more than one cassette (e.g., two cassettes) in the holder without interfering with the ability of the holder to hold a tympanic thermometer at the same time. Consequently, the thermometer system 100 has the capacity to contain a larger supply of probe covers 105 (e.g., at least 22 probe covers and more preferably 32 probe covers) than prior art thermometer systems. The housing 307 is further configured to a pair of aligned, generally U-shaped cutaways 331 in the housing extending down from the upper end 325 of the holder 301 in registration with the grips 271 of the two stacked cassettes 101*a*, 101*b* when the cassettes are received in the holder (FIG. 11). For example, the housing 307 of the holder 301 shown in the drawings defines two cutaways 331, one on each side of the holder in registration with the side walls 127 of the cassettes 101*a*, 101*b*. The cutaways 331 are deep enough to allow the grips 271 of both upper and lower cassettes 101*a*, 111*b*, to be accessed through the cutaways. The cutaways 331 are also preferably wide enough to permit a health care provider to pass at least one finger through each of the cutaways. Other arrangements and configurations of the cutaways are permitted within the scope of the invention.

When the cassettes 101*a*, 101*b* are loaded in the holder 301, there is preferably only a slight separation between the probe covers 105*a*, 105*b* of the upper and lower cassette and also only a slight separation between the probe covers of the lower cassette and their respective wells 305. This, in combination with the frangible connections 157 of the probe covers 105 to the frame 103, helps limit pivotal movement of the probe covers 105 relative to the frame. The probe covers 105*a* of the upper cassette 101*a* can only pivot a relatively small amount relative to the frame 103*a* before the distal end of the probe cover contacts the probe cover 105*b* of the lower cassette with which it is nested. Further pivotal movement of the upper probe cover 105*a* would require movement of the probe 105*b* of the lower cassette with which it is nested. Likewise, the relatively small separation between the probe covers 105*b* of the lower cassette 101*b* and their respective wells 305, in combination with the frangible connections 157 of the probe covers to the frames, limits pivotal movement of the probe covers 105*b* relative to the frame 103*b*. Pivotal movement of the probe cover 105*b* relative to the frame will bring the distal end of the probe cover into contact with the side of the well, which will substantially prevent further pivotal movement of the probe cover. Thus, if the probe of the tympanic thermometer 107 is carelessly inserted into the open end of a probe cover 105 without proper alignment or with a rotational motion that tends to cause pivotal movement of the probe cover relative to the frame, the well 305 (and the probe cover 105*b* of the lower cassette, if the probe cover is attached to the upper cassette 101*a*) will provide additional support against pivotal movement of the probe cover. This helps the user bring the thermometer probe into alignment with the longitudinal axis 141 of the probe cover as required for proper mounting of the probe cover on the thermometer. It also reduces the risk that one of the frangible stems 159 will be broken before the others, which would make it more difficult to mount the probe cover on the thermometer properly. This, in combination with the tapered shape of the probe cover bodies 117, allows a thermometer probe to be inserted into the open end of one of the probe covers to secure the probe cover to the thermometer even when the alignment of the thermometer probe deviates from the longitudinal axis 141 of the probe cover.

The cassettes 101*a*, 101*b* are preferably designed to be used with a particular type of tympanic thermometer 107. This allows the probe covers 105 to be constructed in view of the particular configuration of the thermometer probe 351 so the force required to secure a probe cover to the probe is less than the detachment force required to detach a probe cover from the frame 103. It also allows the frame 103 to be configured to limit movement of the thermometer probe 351 relative to the cassette 101 in the direction of insertion of the probe into one of the probe covers 105.

Figure 16A:
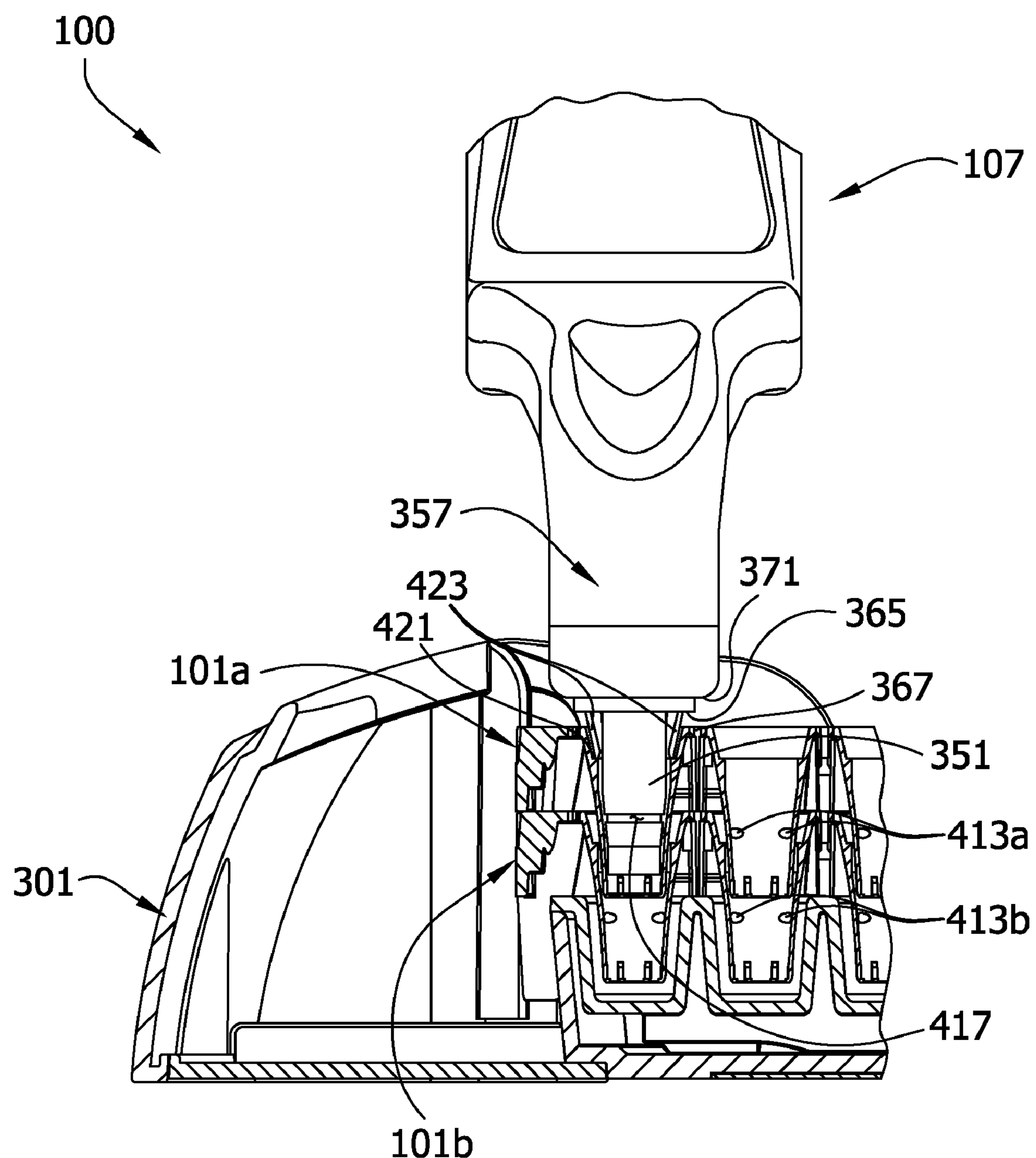
FIGS. 16A-16D are partial, fragmentary sections illustrating a sequence of operation for attaching a probe cover from the upper stacked cassette to the thermometer probe.
Figure 16B:
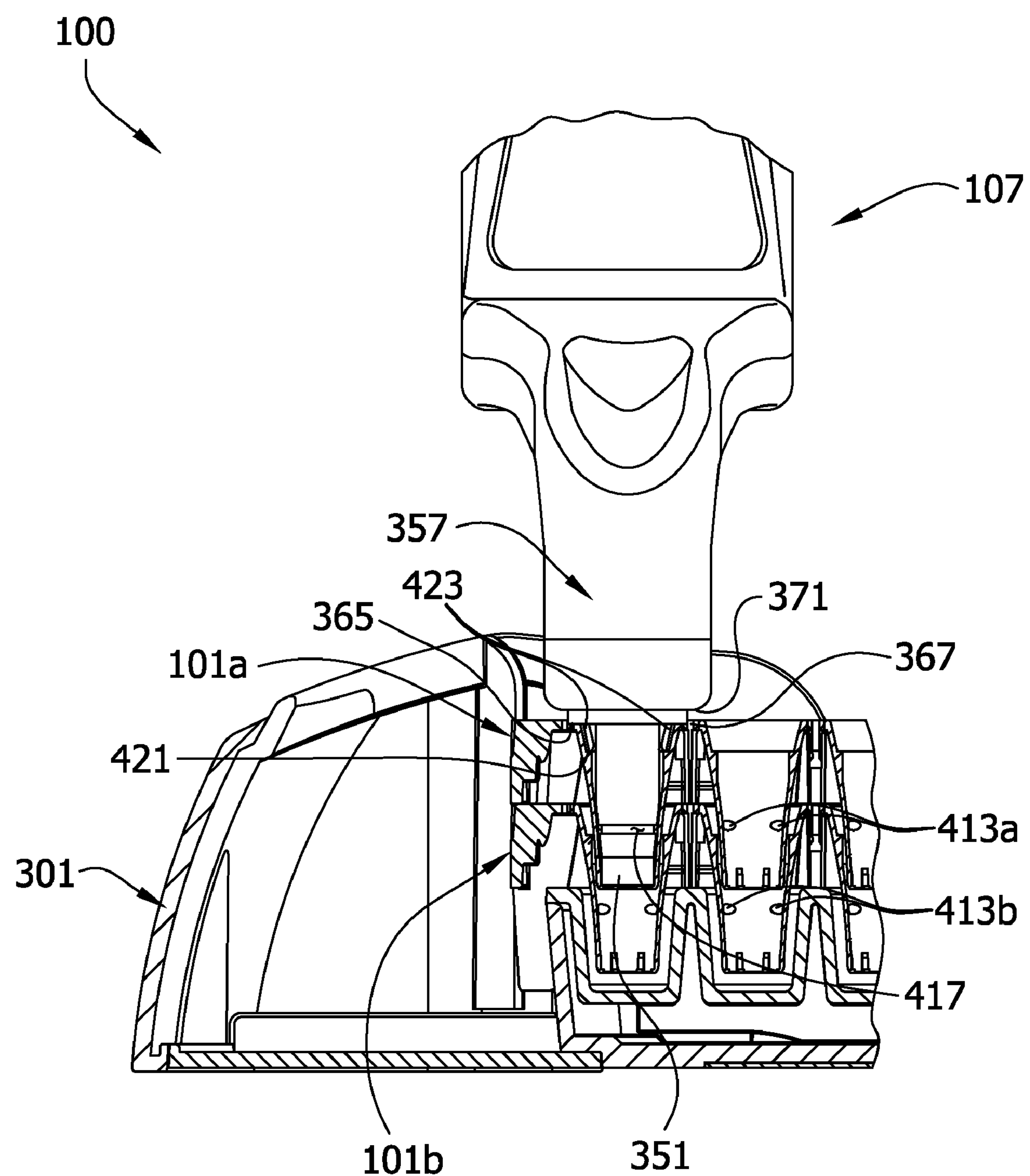
Figure 16C:
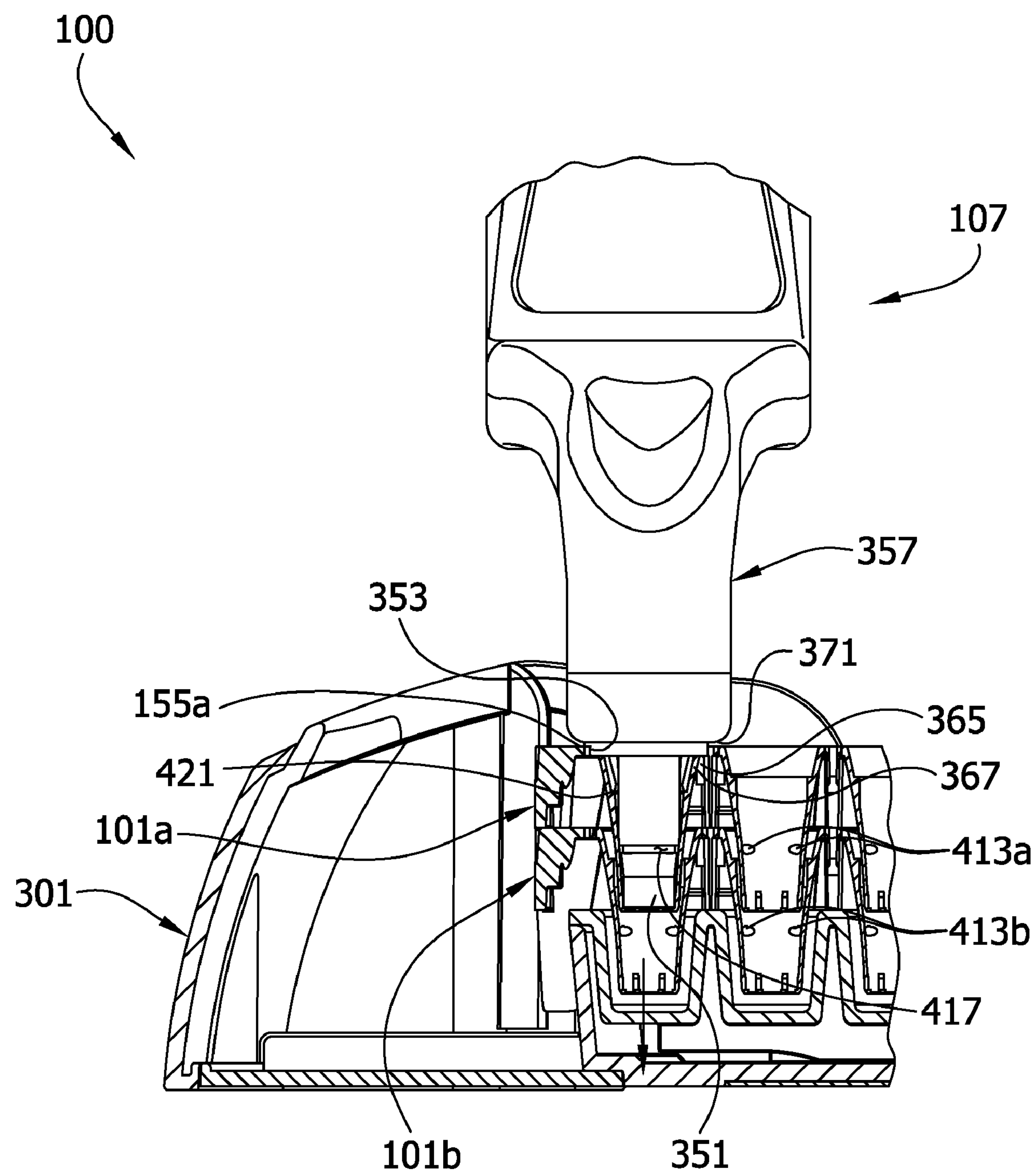
Figure 16D:
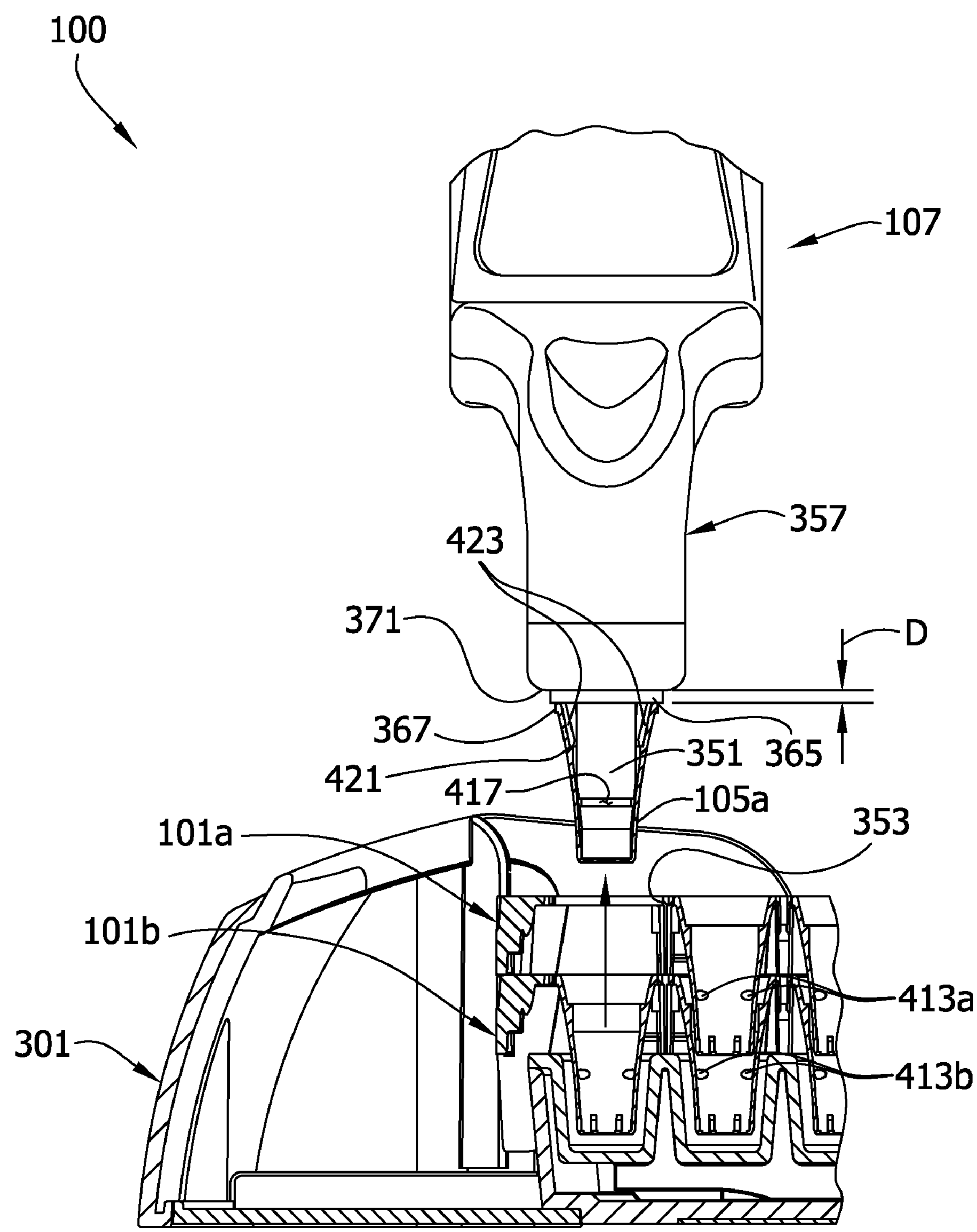
Figure 17A:
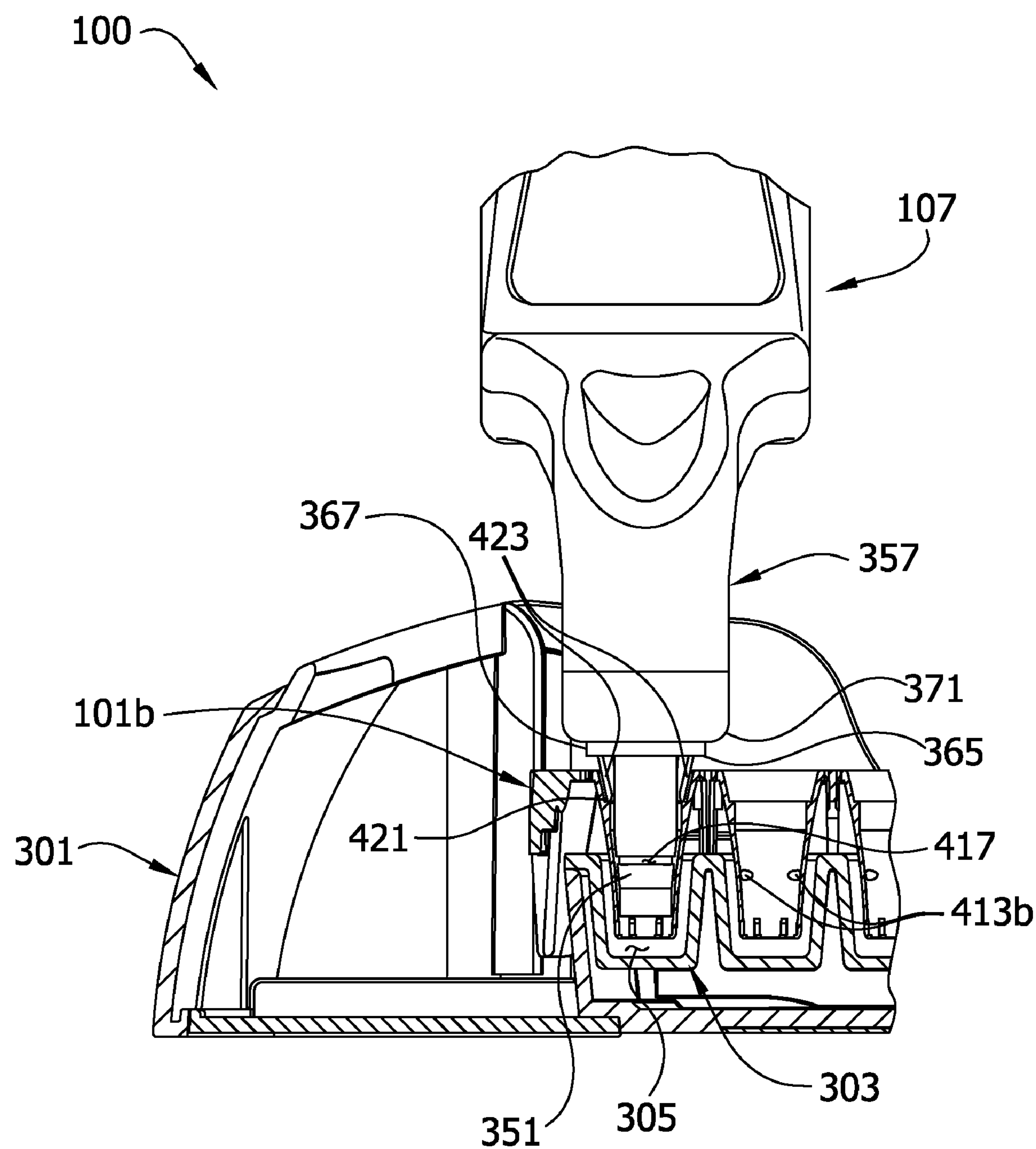
FIGS. 17A-17D are partial fragmentary sections similar to FIGS. 16A-16D illustrating a sequence for attaching a probe cover from the lower cassette to the thermometer probe after the upper stacked cassette has been used and removed from the holder.
Figure 17B:
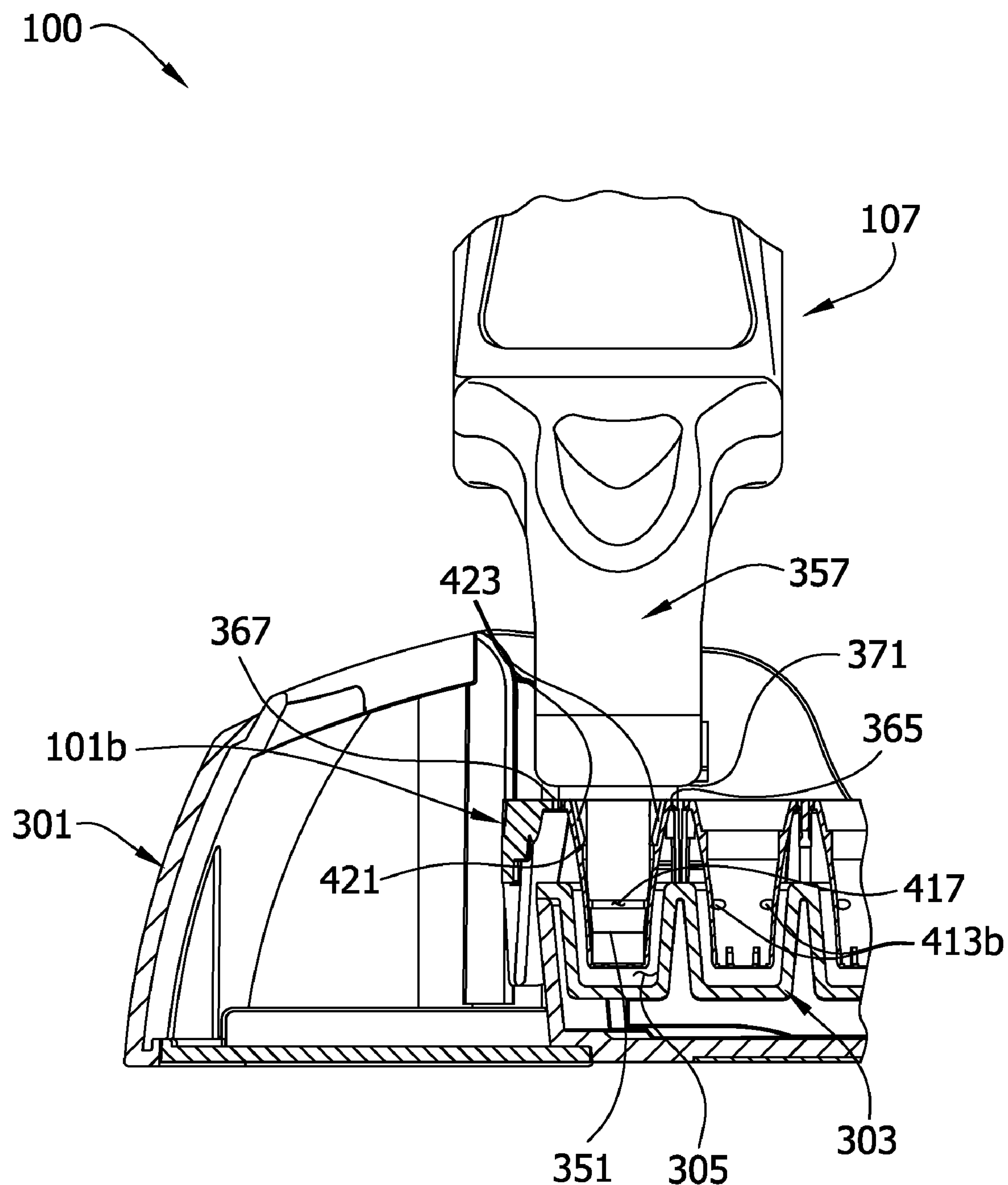
Figure 17C:
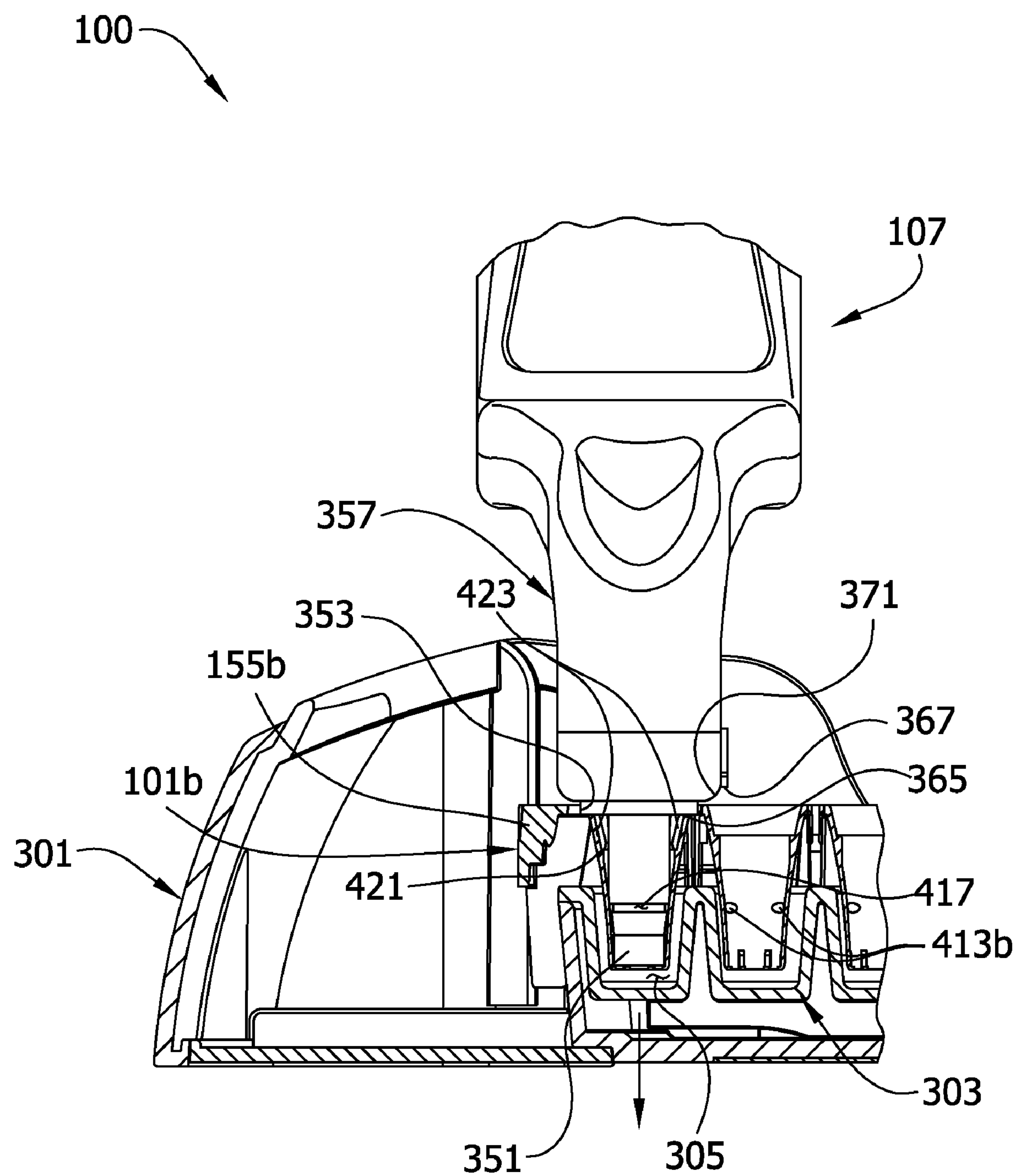
Figure 17D:
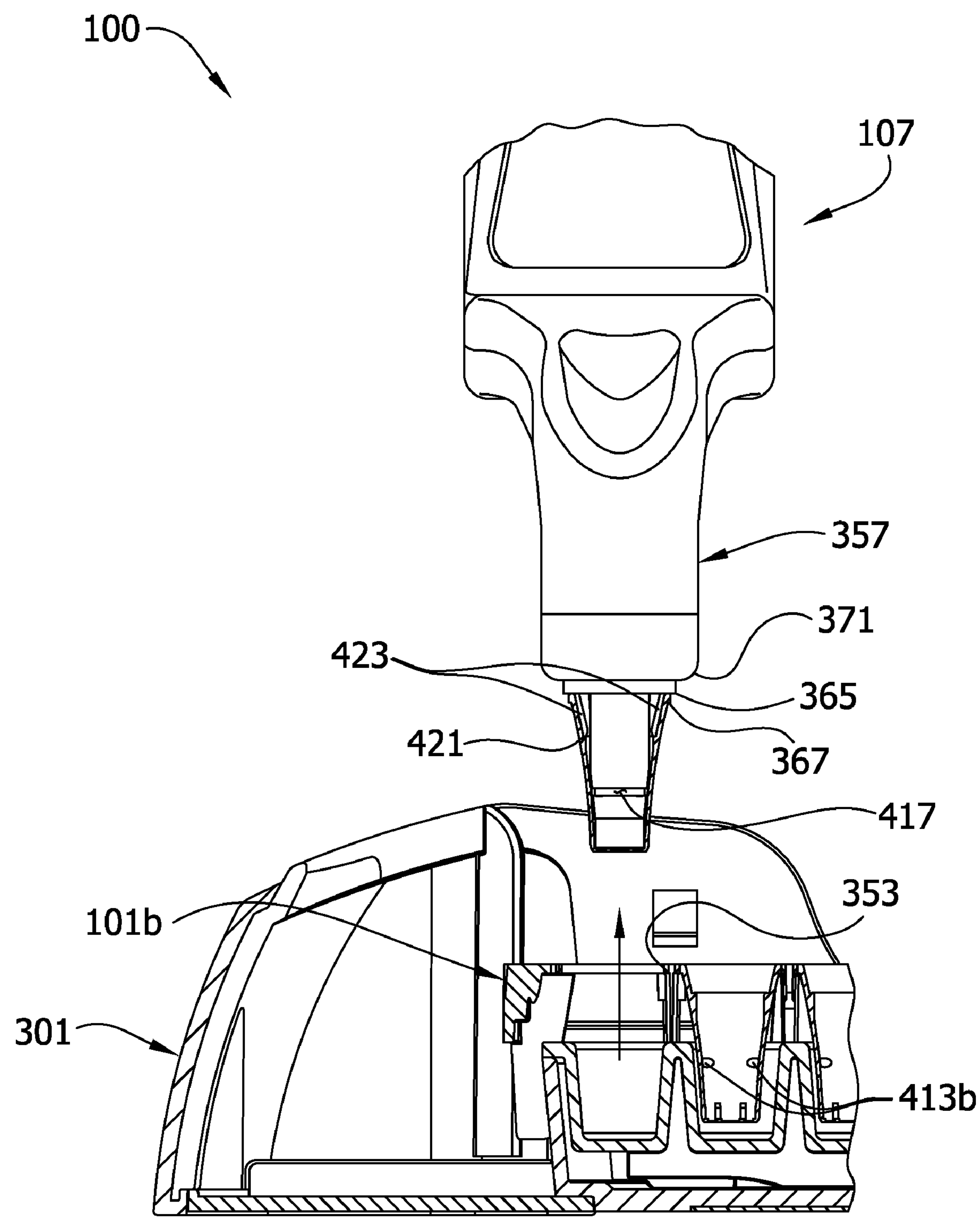

There are many ways to limit movement of the thermometer probe 351 relative to the cassette 101 in the direction of insertion of the probe into one of the probe covers 105. As shown in FIG. 16C for example, an opening 353 is created in the upper surface 155 of the cassette 101 by detachment of a probe cover 105 therefrom. The cassette 101 is configured so that the opening 353 created by removal of one of the probe covers 105 is sized and shaped to permit the distal end of the thermometer 107 to pass through the opening, but to limit the extent to which the distal end of the thermometer can pass therethrough. Preferably, the cassette 101 is configured to substantially prevent one of the probe covers 105*b* on a lower stacked cassette 101*b* from being accidentally detached while the thermometer probe 351 is inserted into a probe cover 105*a* of the upper stacked cassette 101*a* and used to detach the probe cover from the frame 103*a* of the upper cassette. The thermometer 107 shown in the drawings comprises a thermometer probe 351 extending distally from a thermometer body 357. A first ("distal") annular shoulder 365 is formed at the distal end of the thermometer body 357. The first annular shoulder 365 is sized and shaped to abut a proximal end 367 of the probe cover 105 when it is secured over the thermometer probe 351 and still attached to the cassette 101, and then apply the detachment force to the probe cover. Further the first annular shoulder 365 is sized and/or shaped so it can pass through the opening 353 in the cassette 101 created by detachment of a probe cover 105 therefrom. The thermometer body 357 is shaped to form a second ("proximal") annular shoulder 371*a* short distance proximally from the first annular shoulder 365 that abuts the proximal end 367 of the probe cover 105. The first annular shoulder 365 projects distally from the second annular shoulder 371*a* distance D (see FIG. 16D) that is less than the distance between nested probe covers 105*a*, 105*b* of the stacked upper and lower cassettes 101*a*, 101*b*. The circumference of the second annular shoulder 371 is larger than the circumference of the first annular shoulder 365. Further, the second annular shoulder 371 is sized and/or shaped so it will not fit through the opening 353 in the cassette 101 created by detachment of a probe cover 105 from the frame 103. Instead of passing through that opening 353, the second annular shoulder 371 engages the upper surface 155 of the cassette 101 (e.g., the web 171, intermediate longitudinal support 129, and if the detached probe cover is at the end of a row one of the end walls 131), which stops movement of the thermometer 107 in the direction of insertion. The distance D that the first annular shoulder 365 projects from the second annular shoulder 371 is also preferably long enough to facilitate breaking the frangible stems 159, as will be described more fully below. In one embodiment, the distance D is greater than about 1.27 mm (0.05 inches), more preferably the distance D is between about 1.52 mm (0.06 inches) and 2.05 mm (0.081 inches, and most preferably is about 2.05 mm (0.081 inches).

Figure 15:
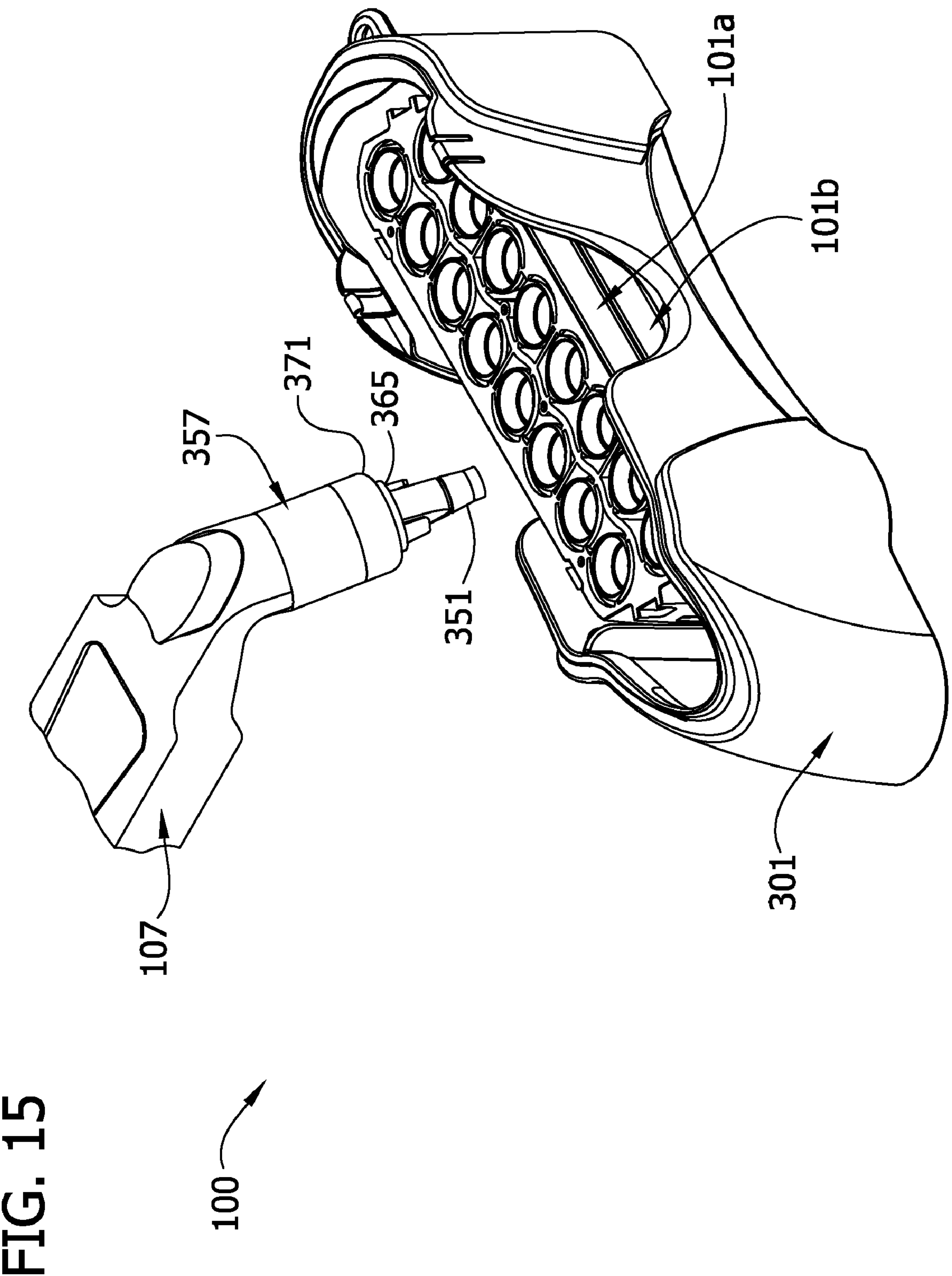
FIG. 15 is a perspective of the thermometer system showing a fragmentary portion of the thermometer about to engage a probe cover of the upper stacked cassette.
Figure 15A:
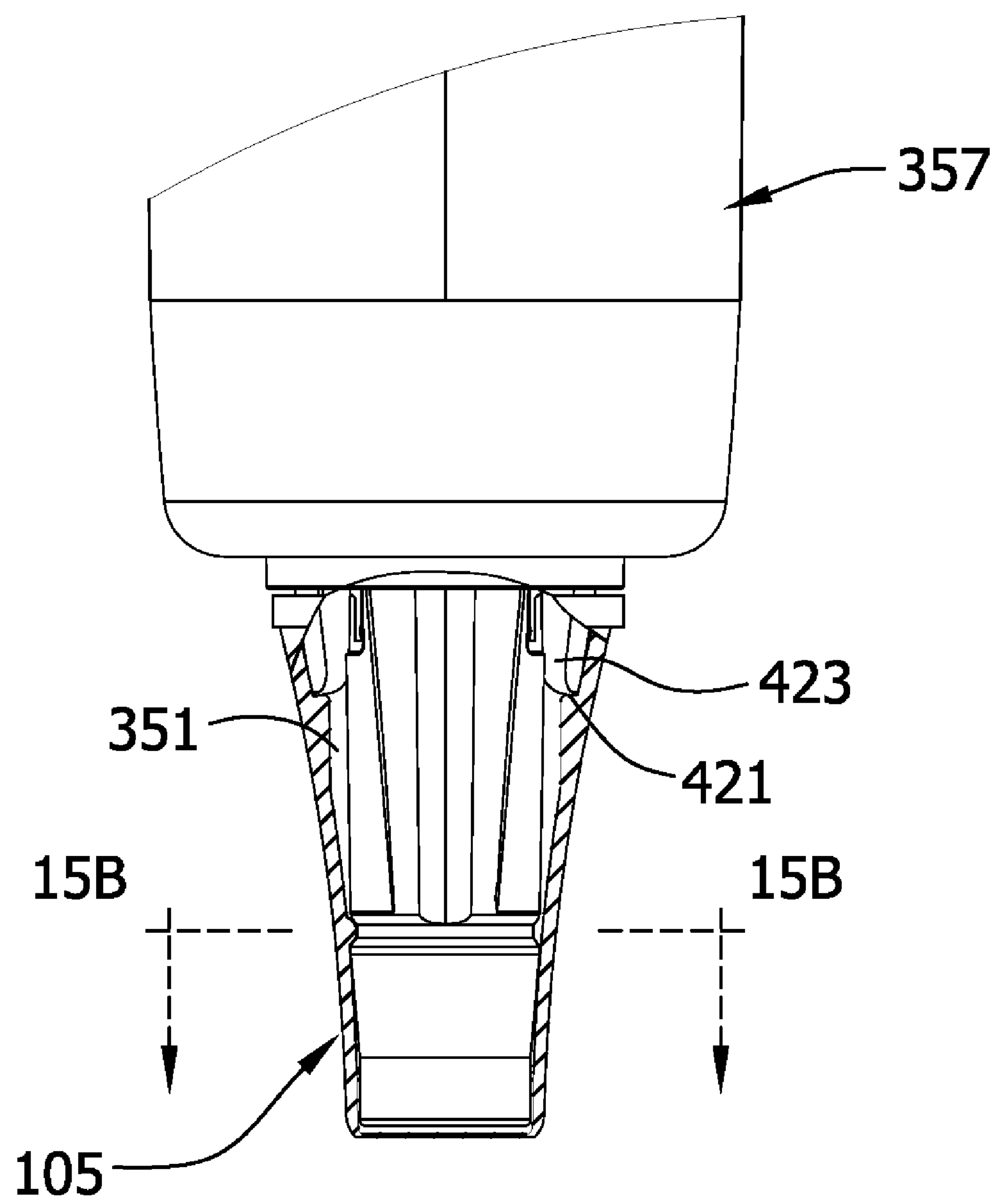
FIG. 15A is a fragmentary section of a probe cover attached to the thermometer probe taken in a plane including a longitudinal axis of the probe cover.

The securement force required to secure a probe cover 105 to the thermometer probe 351 can be reduced by increasing the size of the inside of the probe cover body 117 to reduce resistance to insertion of the thermometer probe therein. The securement force can be affected by various factors. The thermometer 107 shown in FIG. 15A for example, comprises retractable ejection arms 423 designed to engage a shoulder 421 on the probe cover. The ejection arms 423 are typically biased toward an extended position and engage the shoulder 421 as the probe cover 105 is being secured to the probe 351. As the probe 351 is inserted into the probe cover 105, the shoulder 421 pushes the ejection arms 423 against their bias to a retracted position. An actuator (not shown) on the thermometer 107 allows the user to move the ejection arms to their extended position to push the probe cover 105 off the probe 351 after the subject's temperature has been measured. Thus, the amount of force biasing the ejection arms 423 to their extended positions affects the securement force.

Figure 15B:
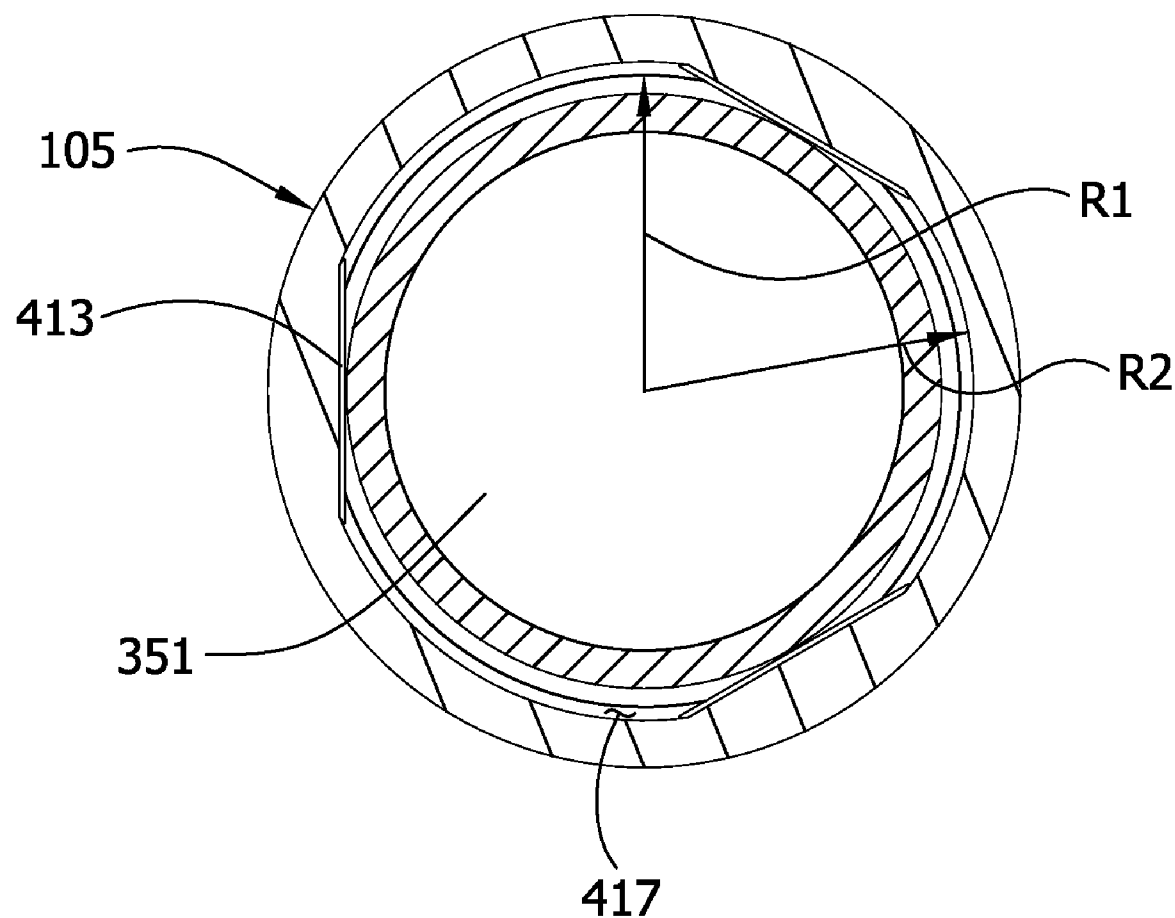
FIG. 15B is a section of the thermometer probe and attached probe cover taken in the plane including line 15B-15B on FIG. 15A.

The securement force is also affected by the friction between the tubular body 117 of a probe cover 105 and the probe 351 and the amount of force (if any) required to deform the probe cover 105 to make it fit on the thermometer probe 351. For example the probe covers 105 shown in FIGS. 15A and 15B have retention bumps 413 (e.g., three retention bumps) on the inside of the probe cover bodies 117. The retention bumps 413 are designed to be received in an annular groove 417 on the thermometer probe 351 when the probe cover 105 is secured to the thermometer probe, thereby helping retain the probe cover on the thermometer probe. In one embodiment, the retention bumps 413 are sized so that an inscribed circle tangent to the apexes of the retention bumps has a radius R1 that in one embodiment is about 0.28 inches (0.71 cm) and the probe 351 is sized so that its radius R2 on the distal side of the groove 417 is about is about 0.30 inches (0.76 cm). The dimensions can be other than described without departing from the scope of the present invention. For this same embodiment, the securement force necessary to attach the probe cover 105 to the probe 351 was found on average to be about 2 lbf (8.9 N). The force required to release the probe cover 105 from the probe 351 was found on average to be about 3 lbf (13.3 N). The detachment force necessary to break the frangible connection 157 and release the probe cover from the frame 103 ranged from about 3.6 lbf (16 N) to about 4.7 lbf (20.9 N). It will be understood that the forces can be other than described without departing from the scope of the present invention.

Another way to design a thermometer system so that the securement force required to secure a probe cover to a thermometer probe is less than the detachment force is to increase the force required to break the frangible connection 157 between the probe cover 105 and the frame. This is easily controlled by those skilled in the art (e.g., by adjusting the thickness and/or number of the frangible stems).

A plurality of cassettes 101*a*, 101*b* may be stacked together in the manner described above and placed in a storage container 111 (e.g., a box as shown in FIG. 1) for shipment and/or storage of a supply of probe covers 105. Stacking the cassettes 101*a*, 101*b* so at least one probe cover 105*a* on one cassette is nested with a probe cover 105*b* of the other cassette, decreases the space required to ship and/or store the cassettes. Preferably, each probe cover 105 of each cassette 101 is nested (either above or below) with a probe cover of another cassette, to make efficient use of space. Although the storage container 111 shown in the drawings is sized to hold two cassettes 101*a*, 101*b*, it is understood that a container could hold many more cassettes, in one or more stacks.

In one embodiment of a method of the present invention, multiple cassettes are stacked together as described above. For example, the cassettes 101*a*, 101*b* may be stacked together at a manufacturing facility and placed in the storage container 111 for shipping. In any event, to stack a pair of cassettes 101*a*, 101*b*, the upper cassette 101*a* is moved relative to the lower cassette 101*b* to a position above the lower cassette. As the upper cassette 101*a* is lowered relative to the lower cassette 101*b*, the aligning systems 221*a*, 221*b* of the cassettes and the tapered bodies 117 of the probe covers 105 facilitate bringing the upper cassette from an orientation relative to the lower cassette that is different from the orientation of the lower cassette into an orientation relative to the lower cassette that is substantially similar to the orientation of the lower cassette. Alignment of the cassettes 101*a*, 101*b* occurs as described previously herein in reference to FIGS. 8 and 8A. Because the probe covers 105 of the upper and lower cassettes 101*a*, 101*b* are supported against pivotal movement relative to the frames 103*a*, 103*b*, there is no need to manually align the individual probe covers for stacking.

As the upper cassette 101*a* is lowered farther relative to the lower cassette 101*b*, the frame 103*a* of the upper cassette engages the frame 103*b* of the lower cassette 101*b* and prevents further movement of the upper cassette toward the lower cassette. At this point stacking of the two cassettes 101*a*, 101*b* is complete and the probe covers 105*a* of the upper cassette 101*a* are held nested within and spaced above the probe covers 105*b* of the lower cassette 101*b*. Additional cassettes can optionally be added to the stack of cassettes if desired. The stack of cassettes 101*a*, 101*b* is loaded into the storage container 111 (optionally with additional stacks of cassettes) and shipped to a health care facility, point of retail sale, or other destination.

In order to use the thermometer system 100, a practitioner takes a plurality of stacked probe cover cassettes (e.g., two cassettes including the upper and lower cassettes 101*a*, 101*b*) out of the storage container 111. The practitioner loads the cassettes 101*a*, 101*b* into the holder 301 by sliding the lips 283 on the sides of the cassettes past the detents 317 of the holder 301 so that the detents are received in the receptacles 281 to snap the lower cassette into the base and to snap the upper cassette into the stacked relation with the lower cassette, as described above. The cassettes 101*a*, 101*b* can be stacked first and then loaded into the holder 301 together or they can be loaded into the holder sequentially. As the cassettes 101*a*, 101*b* snap into place, the user hears an audible click and/or feels a tactilely perceptible pulse when the frame 103*a* of the lower cassette 101*b* contacts the upper surface 311 of the base 303 in the holder 301. Likewise, if the user snaps the upper cassette 101*a* into the holder 103 after the lower cassette 101*b*, the user hears an audible click and/or feels a tactilely perceptible pulse when the frame 103*a* of the upper cassette contacts the upper surface 155*b* of the lower cassette 101*b*. These clicks and/or pulses indicate that the cassettes 101*a*, 101*b* are properly stored in the holder 301. The retaining system 315 of the holder 301 releasably holds the stacked cassettes 101*a*, 101*b* in the holder. Thus, if a probe cover 105 secured to the tympanic thermometer 107 accidentally catches on a frame 103 of the cassette 101 when the thermometer is pulled away from the holder 301, the cassette will be held in place and not pulled out with the probe cover.

Figure 14:
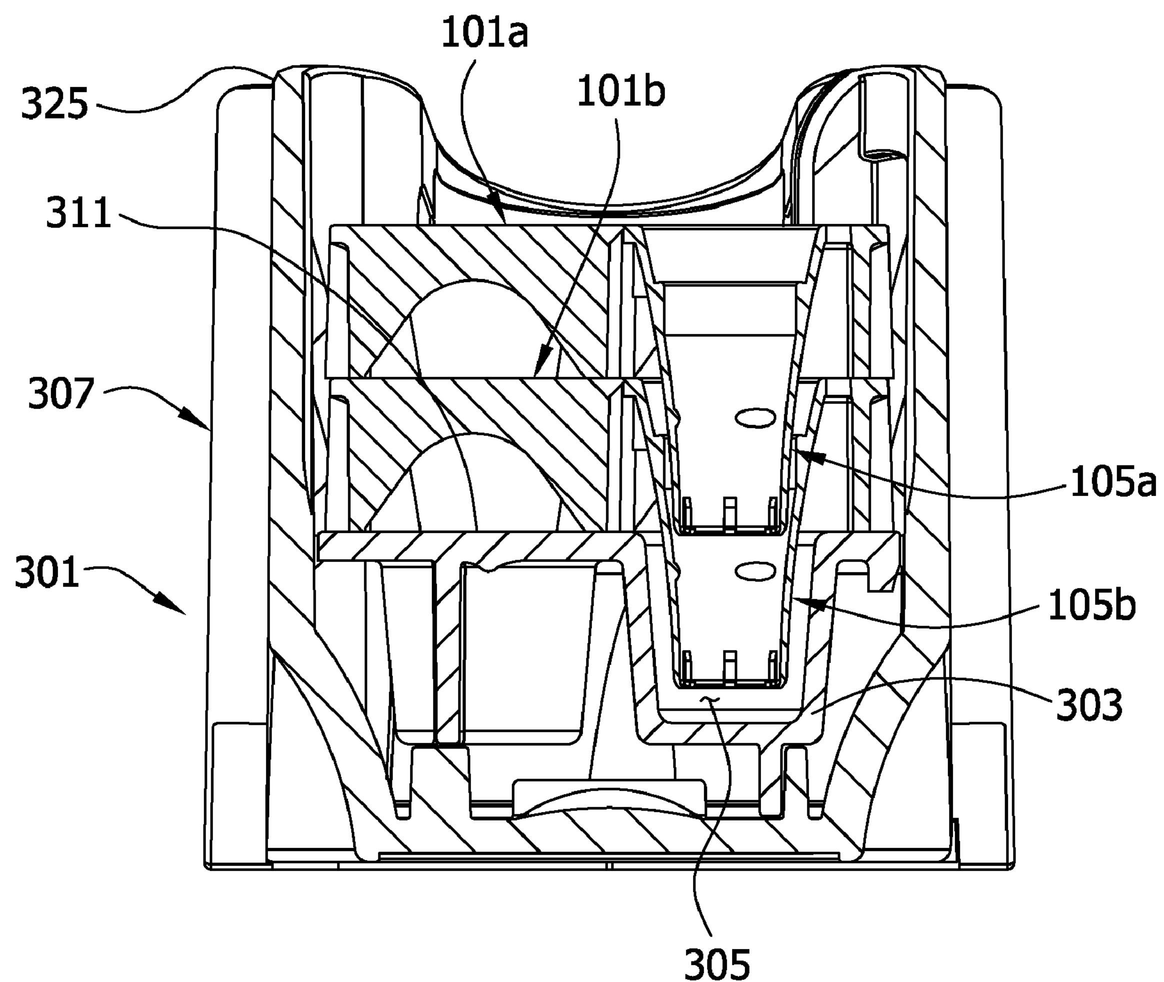
FIG. 14 is a section taken in the plane including line 14-14 of FIG. 12 without the thermometer.

Because the probe covers 105*b* of the lower cassette 101*b* are supported against pivotal movement relative to the frame 103*b* of the lower cassette, there is no need to manually align the probe covers to position them for receipt in the wells 305 of the base 303. Likewise, if the cassettes 101*a*, 101*b* are loaded sequentially, there is no need to manually align the individual probe covers 105*a* of the upper cassette to stack it on top of the lower cassette in the holder 301. After the cassettes 101*a*, 101*b* are loaded in the holder 301, the tympanic thermometer 107 may be placed on the holder 301 on top of the cassettes, as shown in FIGS. 1 and 13-14, until it is needed.

As shown in FIGS. 16A-16D, when the practitioner needs to take the temperature of a subject, he or she removes the thermometer 107 from the holder 301 and inserts the thermometer probe 351 into the opening at the proximal end of one of the probe covers 105*a* of the upper stacked cassette 101*a*. Because the frangible connection 157 resists pivotal movement of the probe cover 105*a* relative to the frame 103*a*, the probe cover tends to urge the thermometer probe 351 into alignment with the probe cover, facilitating insertion of the probe into the probe cover when the probe is slightly out of alignment when the insertion begins. The probe cover 105*a* is secured to the thermometer 107 by applying a securement force to the thermometer probe to snap the retention bumps 413 into the annular groove 417 of the probe 351 and push the ejection arms 423 to their retracted position. Because the securement force is less than the detachment force, the probe cover 105*a* is still attached to the frame 103*a* when it is secured to the thermometer probe 107. Upon securement of the probe cover 105*a* to the thermometer probe 107, the first annular shoulder 365 at the distal end of the thermometer body 357 engages the proximal end 367 of the probe cover 105*a*, thereby substantially preventing further insertion of the probe into the probe cover. As the practitioner continues to exert force tending to move the thermometer 107 in the direction of insertion, the first annular shoulder 365 applies a detachment force to the probe cover 105*a* that breaks the frangible connection 157 between the probe cover and the frame 103*a*, thereby detaching the probe cover from the cassette 101*a*. When the frangible connection 157 breaks, there is an abrupt decrease in resistance to movement of the thermometer 107 in the direction of insertion. The practitioner senses this decrease in resistance. Upon feeling the release of the probe cover 105*a* from the cassette 101*a*, the practitioner knows that the probe cover is fully secured to the thermometer probe 351, that the probe cover has been detached from the cassette, and that the thermometer 107 is ready for use.

Although it is theoretically possible that the practitioner will be able stop movement of the thermometer 107 after release of the probe cover 105*a* from the frame 103*a* before it contacts anything else, most of the time (e.g., absent extraordinary reaction time) the relatively abrupt decrease in resistance to thermometer movement will result in acceleration of the thermometer toward the probe cover 105*b* of the lower cassette 101*b*. However, the thermometer 107 (e.g., the second annular shoulder 371) contacts the frame 103*a* of the upper cassette 101*a* (e.g., the web 171, longitudinal supports 125, and possibly one of the end walls 131 depending on the position of the probe cover 105*a* in its row) upon movement of the thermometer farther in the direction of insertion before either the thermometer or the probe cover secured thereto detach the underlying probe cover 105*b* from the lower cassette 101*b*. The frame 103*a* prevents the thermometer 107 and the probe cover 105*a* secured thereto from moving far enough into the opening to detach or damage the probe cover 105*b* of the lower cassette 101*b*, and preferably prevents the thermometer and the probe cover secured thereto from contacting the underlying probe cover 105*b*. The distance D that the first annular shoulder 365 projects from the second annular shoulder 371 is particularly selected to avoid detaching or damaging the probe cover 105*b* of the lower cassette 101*b*. In the illustrated embodiment, the distance D is about 2.05 mm (0.081 inches). Because the first annular shoulder 365 engages the probe cover 105*a*, it in combination with the engagement of the second annular shoulder 371 with the frame 103*a* controls the length of movement of the probe cover 105*a* downward toward the second probe cover 105*b*. However, the distance D has also be carefully selected to be long enough to produce a sufficient deformation of the frangible stems 159 to assure breakage of the probe cover 105*a* away from the frame 103*a* without requiring twisting of the probe cover or other extraneous action. The material of the cassettes 101*a*, 101*b* tends to stretch so that unless the stems 159 are deformed enough, breakage of the stems cannot be certain. For this reason, the distance D of the first annular shoulder 365 has been selected to be as great as possible without affecting the probe cover 105*b* of the lower cassette 101*b*.

Contact of the second annular shoulder 371 of the thermometer 107 with the frame 103*a* after detachment of the probe cover 105*a* from the first cassette 101*a* produces an audible click and/or a tactilely perceptible pulse, which indicates that the probe cover 105*a* is detached from the cassette 101*a* and successfully secured to the probe of the thermometer 107. The stiffness of the frame 103*a* enhances its ability to withstand the securement force, the detachment force, and the impact force when the thermometer 107 engages the frame after detachment of the probe cover 105*a* therefrom without damaging or releasing any of the other probe covers 105*a*, 105*b* of either cassette 101*a*, 101*b* with only minimal or no external support.

The thermometer 107 is then used to take the subject's temperature with the probe cover 105*a* providing a sanitary barrier between the subject and the thermometer probe. After use with one subject, the probe cover 105*a* is removed from the thermometer probe 107 and discarded. When the practitioner needs to take another subject's temperature, he or she repeats the process with another probe cover 105*a* of the upper cassette 101*a*. When all the probe covers 105*a* of the upper cassette 101*a* have been used and discarded, the practitioner grips the upper cassette by its grip 271*a* through the cutaways 331 in the housing 307 of the holder 301. Although this is not believed to be necessary in the illustrated embodiment, the practitioner may also grip the lower cassette 101*b* by its grip 271*b* through the cutaways 331 in the housing 307 to hold it in the holder 301. However, it may not be necessary to hold the underlying lower cassette 101*b* if the retaining system 315 and/or gravity provide sufficient force to separate the cassettes 101*a*, 101*b*. Either way, the practitioner pulls the upper cassette 101*a* out of the holder 301 by its grip 271*a* and discards the now empty cassette.

To take the temperature of the next subject, the practitioner inserts the thermometer probe 107 into one of the probe covers 105*b* of the lower cassette 101*b*, secures it to the probe, and detaches it from the frame 103*b* in substantially the same way as was done for the upper cassette 101*a*, as shown in FIGS. 17A-17D. Because there are no underlying probe covers, there is no need to worry that the thermometer 107 will accidentally detach or damage any underlying probe covers upon release of the probe cover 105*b* from the frame 103*b*. However, it is desirable to prevent the distal end of the thermometer probe 107 and the probe cover 105*b* attached thereto from contacting the bottom of the well 305 because that would be hard on the thermometer probe and might damage the film 115 of the probe cover. However, the frame 103*b* of the lower cassette 101*b* engages the thermometer 107 in substantially the same way as the frame 103*a* of the upper cassette 101*a* to limit movement of the thermometer in the direction of insertion after detachment of the probe cover and produces an audible click indicating that the probe cover 105*b* is detached from the lower cassette 101*b* and successfully secured to the probe of the thermometer 107. Thus, the upper surface 155*b* of the lower cassette 101*b* also stops movement of the thermometer 107 in the direction of insertion before the distal end of the thermometer probe and/or the probe cover 105*b* secured thereto contact the bottom of the well 305.

When all the probe covers 105*b* of the lower cassette 101*b* have been used and discarded, the practitioner grips the lower cassette by its grip 271*b* through the cutaways 331 in the housing 307 and pulls the lower cassette out of the holder 301. The now empty lower cassette 101*b* is then discarded. The practitioner may then get another set of cassettes out of the storage container 111 (or another container) and snap them into the holder 301 to repeat the process.

The probe covers of a cassette can vary from the probe covers shown in the exemplary embodiment shown and described above. For example, the probe covers can be constructed from other materials. Further, the probe covers can be constructed to have a different configuration from the probe covers of the exemplary embodiment. If desired, the film portion of the probe covers can be integrally formed as one piece with the body rather than a film that is formed separately from the body. Virtually any probe cover manufactured in an injection molding process can be releasably attached to a frame to form a cassette that is within the scope of the present invention.

The frame can have virtually any configuration the permits releasable attachment of a plurality of probe covers thereto without departing from the scope of the invention. For example, the probe covers can be arranged differently, such as in rows differing in number or orientation from the embodiment described above, in other geometric configurations (e.g., a hexagonal pattern), and/or without being organized in any rows without departing from the scope of the invention. Moreover, the probe covers can be positioned laterally of the frame (e.g., on the outside of the cassette) without departing from the scope of the invention.

Further, the exemplary cassette shown and described above comprises a plurality of reinforcing structures (e.g., the web, cross braces, flanges and the plurality of intersections of three substantially orthogonal walls thereof) which are arranged to provide stiffness to the frame of the cassette. It is recognized that some or all of these features can be omitted without departing from the scope of the invention. Likewise, different reinforcing structures and/or a different arrangement of reinforcing structures can be used to stiffen the frame if desired without departing from the scope of the invention. Further, it is possible to obtain many advantages of the invention without any stiffness enhancing features being included in the frame.

The guide wedge of the particular aligning system shown in the drawings its narrower at its top and the notch is wider end at its bottom, however, it is possible to construct an aligning system having a wedge that is narrower at its bottom and a notch that is wider at its top without departing from the scope of the invention. Likewise, it is not necessary to have the aligning system at the end of the cassette.

Although the exemplary method shown and described above involves stacking multiple cassettes that are substantially identical to each other, it is contemplated that one or more cassettes in a stack of cassettes could be different from one or more other cassettes in the stack without departing from the scope of the invention. For example, one cassette (e.g., a cassette intended to be on the bottom of a stack) could be constructed differently to facilitate that cassette's ability to perform a particular function that is not required of all the cassettes (e.g., to engage a base that receives the stack of cassettes). Moreover, some advantages of the invention could be attained by stacking one or more different sized cassettes on top of a lower cassette without departing from the scope of the invention. Further, it is possible to obtain some of the benefits of the invention (e.g., the more pronounced tactile feedback while inserting a thermometer probe into a probe cover and detaching the probe cover from the frame) without any stacking.

Accordingly, it will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A cassette comprising a frame and a plurality of tympanic thermometer probe covers, each of the probe covers being releasably attached to the frame by at least three frangible connections, said at least three frangible connections constructed to allow the respective probe cover to be detached from the frame upon application of a detachment force that breaks the frangible connections, the frangible connections being arranged to support the respective probe cover against pivoting relative to the frame when the probe cover is releasably attached to the frame.

2. A cassette as set forth in claim 1, wherein said at least three frangible connections comprise at least three frangible stems connecting the respective probe cover to the frame at different locations.

3. A cassette as set forth in claim 2, wherein the frangible stems are spaced apart from one another around a circumference of the respective probe cover.

4. A cassette as set forth in claim 1, wherein the frame comprises a plurality of longitudinal supports supporting a plurality of probe covers arranged in a row, the frame further comprising at least one cross brace connecting the longitudinal supports between two of the probe covers.

5. A cassette as set forth in claim 1, the probe covers being arranged in at least one row, the cassette comprising a plurality of stiffness enhancing supports, said plurality of supports including at least two longitudinal supports extending generally in the direction of said at least one row and at least one cross brace connecting the at least two longitudinal supports, said at least one cross brace being positioned between two of the releasably attached probe covers in said at least one row to resist deflection of the frame when the probe covers are detached from the frame.

6. A cassette as set forth in claim 5, wherein the frame further comprises a web extending laterally from one of the longitudinal supports, the web, cross brace and longitudinal support intersecting at a location, each of the web, cross brace and longitudinal support being oriented in a different plane at said location.

7. A cassette as set forth in claim 6, wherein each of the web, cross brace and longitudinal support are mutually orthogonal to one another at said location.

8. A cassette as set forth in claim 1, wherein the frame comprises a side wall and a web projecting inwardly of the side wall, the web including at least one spur projecting generally between adjacent probe covers, at least one of the frangible connections extending from the spur to one of the adjacent probe covers.

9. A cassette as set forth in claim 1, wherein the probe covers comprise tubular bodies having an opening at a proximal end thereof for receiving the probe of a tympanic thermometer and a film-covered infrared-transparent window at a distal end thereof for permitting radiation from a subject's tympanic membrane to pass through the window to the probe.

10. A cassette as set forth in claim 1, wherein the frame comprises a cassette aligning system that facilitates bringing a substantially identical cassette into substantial alignment with and into a substantially similar orientation as the cassette when the cassette and said substantially identical cassette are being stacked on one another.

11. A cassette as set forth in claim 1, wherein the cassette is configured for stacking with another substantially identical cassette in either of two different orientations, such that the probe covers of the cassette and said substantially identical cassette are nested with one another in either of said two orientations.

* * * * *